(12) United States Patent
Santhanam et al.

(10) Patent No.: US 9,786,092 B2
(45) Date of Patent: Oct. 10, 2017

(54) PHYSICS-BASED HIGH-RESOLUTION HEAD AND NECK BIOMECHANICAL MODELS

(71) Applicant: THE REGENTS OF THE UNIVERSITY OF CALIFORNIA, Oakland, CA (US)

(72) Inventors: Anand P. Santhanam, Culver City, CA (US); John Neylon, Los Angeles, CA (US); Patrick A. Kupelian, Los Angeles, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 15/047,580

(22) Filed: Feb. 18, 2016

(65) Prior Publication Data
US 2016/0247312 A1    Aug. 25, 2016

Related U.S. Application Data

(60) Provisional application No. 62/117,836, filed on Feb. 18, 2015.

(51) Int. Cl.
| | |
|---|---|
| *G06T 15/08* | (2011.01) |
| *G06T 15/00* | (2011.01) |
| *G06T 11/00* | (2006.01) |
| *A61B 34/10* | (2016.01) |
| *G06T 7/33* | (2017.01) |

(52) U.S. Cl.
CPC ............ *G06T 15/08* (2013.01); *A61B 34/10* (2016.02); *G06T 7/33* (2017.01); *G06T 11/008* (2013.01); *A61B 2034/105* (2016.02); *G06T 2207/10081* (2013.01); *G06T 2207/30004* (2013.01); *G06T 2207/30008* (2013.01); *G06T 2211/40* (2013.01)

(58) Field of Classification Search
None
See application file for complete search history.

(56) References Cited

U.S. PATENT DOCUMENTS

| | | | | |
|---|---|---|---|---|
| 6,112,112 A * | 8/2000 | Gilhuijs | .................... | G06T 7/11 378/37 |
| 2004/0247074 A1* | 12/2004 | Langton | .................. | G06T 17/20 378/54 |
| 2005/0119568 A1* | 6/2005 | Salcudean | ................ | A61B 8/08 600/437 |
| 2006/0239577 A1* | 10/2006 | Piatt | .................... | G06F 19/3437 382/254 |
| 2009/0148012 A1* | 6/2009 | Altmann | .............. | A61B 6/5247 382/128 |

(Continued)

OTHER PUBLICATIONS

Al-Mayah, et al. "Biomechanical-based image registration for head and neck radiation treatment." Physics in medicine and biology 55.21 (2010): 6491.*

(Continued)

*Primary Examiner* — Saptarshi Mazumder
(74) *Attorney, Agent, or Firm* — O'Banion & Ritchey LLP; John P. O'Banion

(57) ABSTRACT

Systems and methods are shown for developing physics-based high resolution biomechanical head and neck deformable models for generating ground-truth deformations that can be used for validating both image registration and adaptive RT frameworks.

24 Claims, 16 Drawing Sheets

(56) References Cited

U.S. PATENT DOCUMENTS

2014/0057236 A1* 2/2014 Meglan ............... G09B 23/28
434/268

OTHER PUBLICATIONS

Sarrut "Deformable Registration for Image-Guided Radiation Therapy", Zeitschrift für medizinische Physik 16.4 (2006): 285-297.*
Harada "Chapter 29. Real-Time Rigid Body Simulation on GPUs", GPU Gems 3, Addison-Wesley Professional (Aug. 12, 2007).*
Kavan et al. "Dual Quaternions for Rigid Transformation Blending", Trinity College Dublin, Tech. Rep. TCD-CS-2006-46 (2006).*
Men et al. "GPU-based ultra-fast direct aperture optimization for online adaptive radiation therapy", Physics in Medicine and Biology 55.15 (2010): 4309.*

* cited by examiner

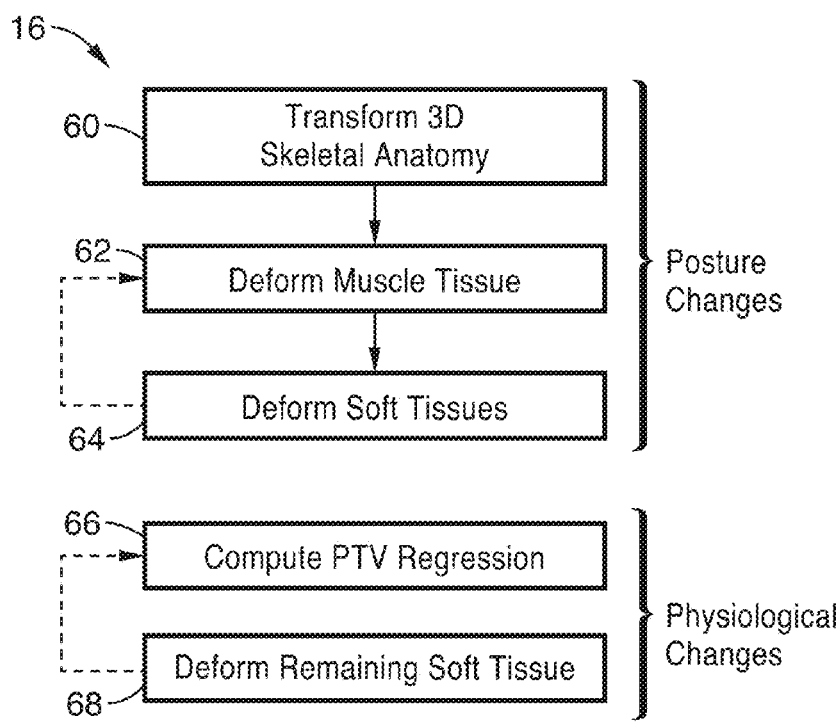
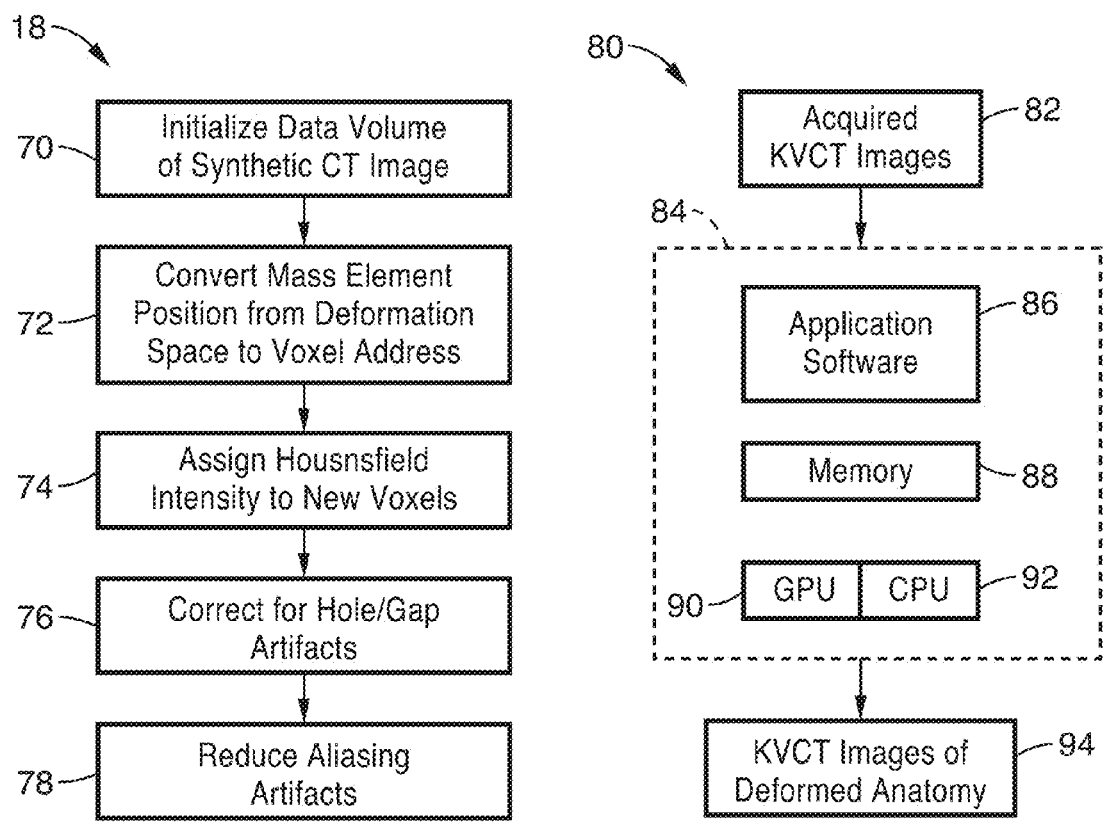

PHYSICS-BASED HIGH-RESOLUTION HEAD AND NECK BIOMECHANICAL MODELS

CROSS-REFERENCE TO RELATED APPLICATIONS

This application claims priority to, and the benefit of, U.S. provisional patent application Ser. No. 62/117,836 filed on Feb. 18, 2015, incorporated herein by reference in its entirety.

STATEMENT REGARDING FEDERALLY SPONSORED RESEARCH OR DEVELOPMENT

Not Applicable

INCORPORATION-BY-REFERENCE OF COMPUTER PROGRAM APPENDIX

Appendix A referenced herein is a computer program listing in a text file entitled "UC_2014_643_3_LA_US_appendix_A.txt" created on Feb. 18, 2016 and having a 348 kb file size. The computer program code, which exceeds 300 lines, is submitted as a computer program listing appendix through EFS-Web and is incorporated herein by reference in its entirety.

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND

1. Technical Field

This description pertains generally to deformable image registration, and more particularly to deformable image registration for head and neck anatomy.

2. Background Discussion

The term head and neck cancer (HNC) refers to a group of biologically similar cancers originating from the upper aero digestive tract, including the lip, oral cavity (mouth), nasal cavity, Para nasal sinuses, pharynx, and larynx. 90% of head and neck cancers are squamous cell carcinomas (SCCHN), originating from the mucosal lining (epithelium) of these regions. HNC often spread to the lymph nodes of the neck, leading to cancer metastasis in the rest of the patient's body. Radiotherapy (RT) has seen a major push towards treatment plans for the HNC that are tailored to the patient and adapted to their radiation response. Ignoring patient misalignments caused by non-rigid changes in patient posture and physiology can lead to under-dosing the tumor and over-irradiating the healthy tissue. Image-guided analyses of such non-rigid head and neck anatomy variations were made possible by use of deformable image registration (DIR) frameworks that register the patient planning anatomy with the treatment anatomy. Such analyses have led to several indications on the need for better patient aligning. For instance, it has been shown that uncorrected patient positioning misalignments would increase the maximum dose to both the brainstem and spinal cord by 10 Gy and the mean dose to the left and right parotid glands by 7.8 and 8.5 Gy, respectively. Similarly, 95% of the gross tumor volume (GTV) and clinical target volume (CTV) would decrease by 4 Gy and 5.6 Gy, respectively.

The accuracy of DIR to help quantify patient posture and physiological changes is instrumental for the success of adaptive RT. Adaptive RT employs quantitative dose delivery error characterization and subsequent compensatory strategies. However, DIR development has been hampered by a lack of techniques that generate ground-truth deformations that can be used to evaluate competing DIR algorithms. Biomechanical human anatomy models have been developed for applications ranging from computer animation to CT image registration.

Sophisticated biomechanical models have been developed for individual anatomical sites, including the head and neck, the hand, lungs, and the leg. Such models, when developed from patient CT or MRI, can create subject-specific physiological and musculoskeletal dynamic atlas. As an example, subject specific cardiac models of normal and diseased heart have been developed using Non-Uniform Rational Bezier Splines (NURBS) in order to simulate the cardiac motion before and after the treatment. Physics-based methods, such as Finite Element Methods and Mass-Spring Models, have been applied for deforming anatomy of the torso, and the biomechanical nature of these models also allows for the inclusion of subject specific tumor representations and day-to-day variations in the treatment.

BRIEF SUMMARY

The technology of the present description comprises a biomechanical model for generating ground-truth deformations that can be used for validating both image registration and adaptive RT frameworks. The systems and methods of the present description validate the usage of deformable image registration (DIR) for daily patient positioning for adaptive radiotherapy applications pertaining to head and neck (HN) radiotherapy. Methodology is provided for generating biomechanically realistic ground-truth data for validating DIR algorithms for HN anatomy by developing a high-resolution deformable biomechanical HN model from a planning CT, simulating deformations for a range of inter-fraction posture changes and physiological regression, and generating subsequent CT images representing the deformed anatomy.

In one exemplary embodiment, the biomechanical model is generated using HN kVCT datasets and the corresponding structure contours. The voxels inside a given 3D contour boundary are clustered using a GPU-based algorithm that accounts for inconsistencies and gaps in the boundary to form a volumetric structure. While the bony anatomy is modeled as rigid body, the muscle and soft tissue structures are modeled as mass-spring-damper (MSD) models with elastic material properties that corresponded to the underlying contoured anatomies. Within a given muscle structure, the voxels are classified using a uniform grid and a normalized mass is assigned to each voxel based on its Hounsfield number.

In one embodiment, the soft-tissue deformation for a given skeletal actuation is performed using an implicit Euler integration with each iteration split into two sub-steps: one for the muscle structures, and the other for the remaining soft tissues. Posture changes are simulated by articulating the skeletal structure and enabling the soft structures to deform accordingly. Physiological changes representing tumor regression were simulated by reducing the target volume and enabling the surrounding soft structures to deform accordingly.

The biomechanical model anatomy is preferably generated using a head and neck kVCT dataset and the corresponding critical structure contours. Accuracy and stability of the model response were validated using ground truth simulations representing soft tissue behavior under local and global deformations. The voxels inside a given 3D contour boundary are clustered using a GPU-based algorithm that accounts for inconsistencies (e.g. anti-aliasing artifacts) and gaps in the contour boundary to form a deformable volumetric structure. Numerical accuracy of the HN deformations are analyzed by applying non-rigid skeletal transformations acquired from inter-fraction kVCT images to the model's skeletal structures and comparing the subsequent soft tissue deformations of the model with the clinical anatomy. While the bony anatomy is modeled as rigid body, the contoured muscle and soft tissue structures are modeled as mass spring models with elastic material properties that corresponded to the underlying contoured anatomies. Within a given muscle structure, the voxels are classified using a uniform grid and a normalized mass assigned to each voxel based on the voxel's Hounsfield number.

The GPU based framework of the present technology enables the model deformation to be performed at 60 frames per second, facilitating simulations of posture changes and physiological regressions at interactive speeds. The soft tissue response of the model is accurate with an $R^2$ value of >0.98 when compared to ground-truth global and local force deformation analysis. The deformation of the HN anatomy by the model agrees with the clinically observed deformations with an average correlation coefficient of 0.956. For a clinically relevant range of posture and physiological changes, the model deformations stabilize with an uncertainty of less than 0.01 mm.

Documenting dose delivery for HN radiotherapy is essential accounting for posture and physiological changes. The biomechanical model discussed herein is able to deform in real-time, allowing interactive simulations and visualization of such changes. The model allows for patient specific validations of the DIR method and has the potential to be a significant aid in adaptive radiotherapy techniques.

The models of the present description comprise a number of unique features, including: a) a high-resolution representation having each of its elements representing a volume of less than 1 cubic mm; b) the ability to run on a single GPU or multi GPU deformation framework, thereby facilitating greater than 15 deformation frames per second; c) generation of subsequent CT images representing the deformed anatomy; and d) the ability to shrink and expand substructures inside the head and neck anatomy (parotid glands, muscle structures, etc.) to represent anatomical changes for both animation purposes and medical treatment planning purposes.

Further aspects of the technology will be brought out in the following portions of the specification, wherein the detailed description is for the purpose of fully disclosing preferred embodiments of the technology without placing limitations thereon.

BRIEF DESCRIPTION OF THE SEVERAL VIEWS OF THE DRAWING(S)

The technology described herein will be more fully understood by reference to the following drawings which are for illustrative purposes only.

Figure 4A:
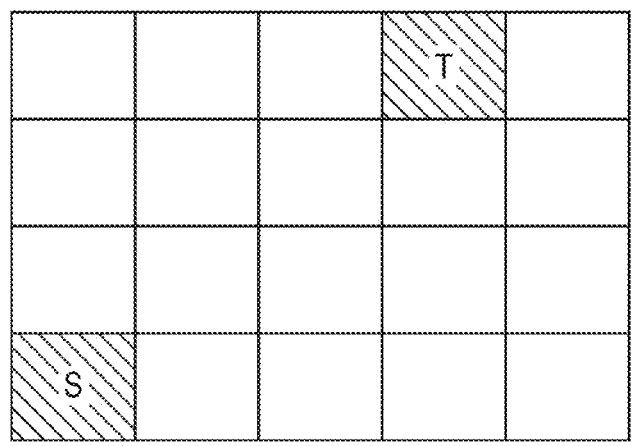
Figure 4B:
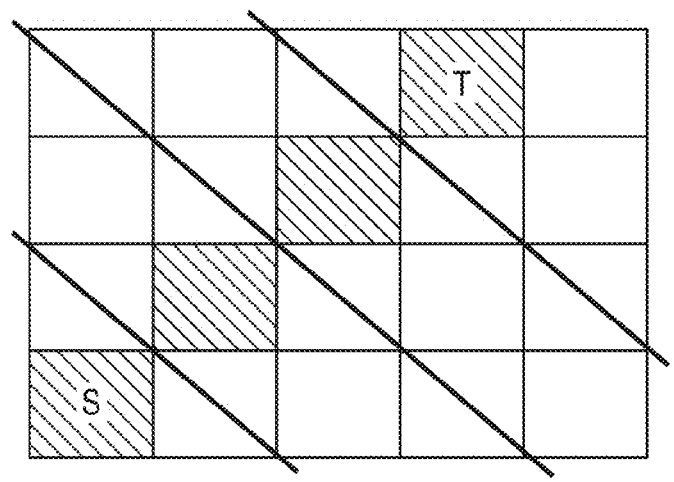
Figure 4C:
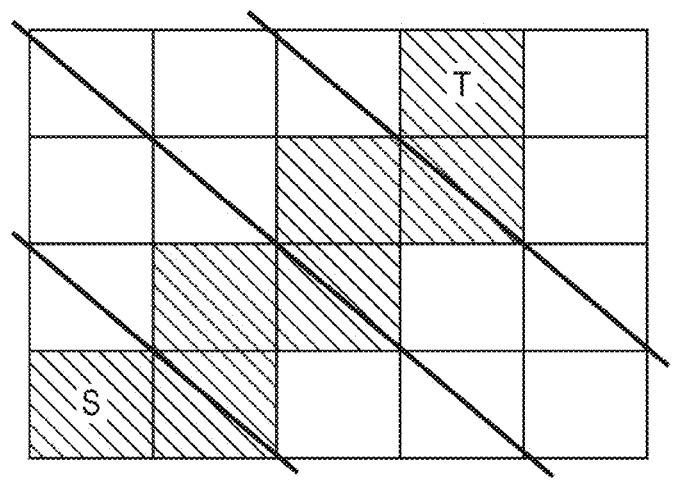

FIG. 4A through FIG. 4C show schematic diagrams illustrating the contour-filling algorithm in accordance with the present description. FIG. 4A depicts two contour boundary points S and T. FIG. 4B illustrates connecting the boundary points using a Bresenham's line generating algorithm. FIG. 4C illustrates connecting the boundary points and filled contour structure using the method of the present description.

Figure 2:
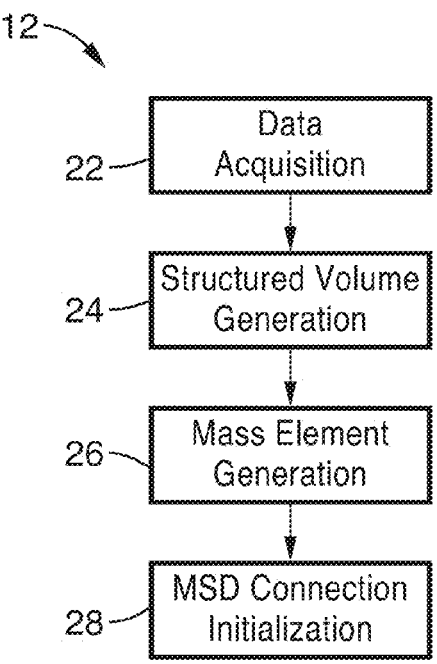
FIG. 2 shows a schematic flow diagram for the step of generating a model shown in the flow diagram of FIG. 1.
Figure 5:
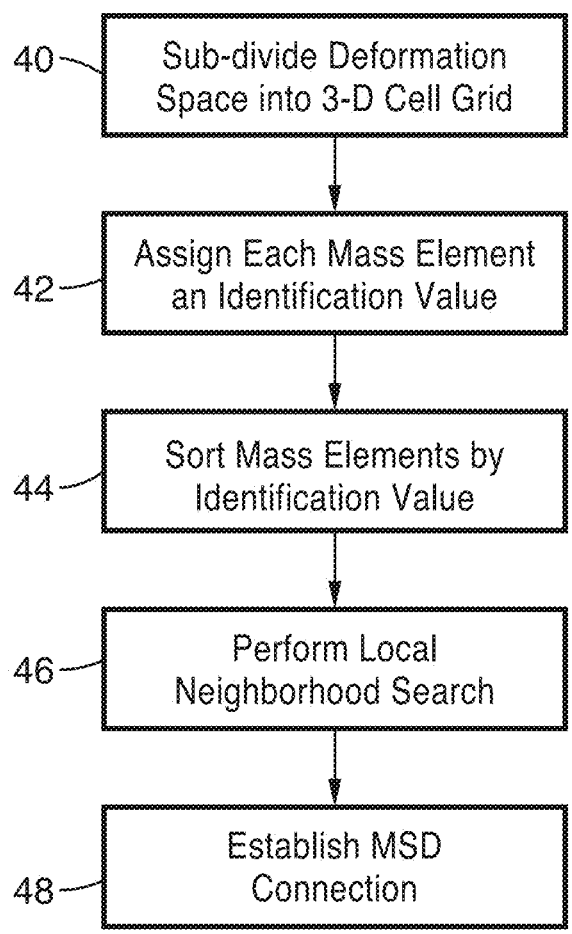

FIG. 5 shows a detailed flow diagram for the MSD connection validation step of FIG. 2.

Figure 6:
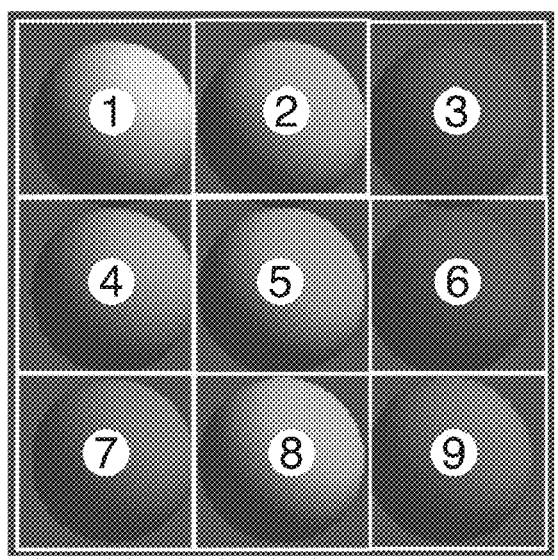

FIG. 6 shows a schematic illustration of sub-dividing the deformation space into a 3D uniform cell grid.

Figure 7:
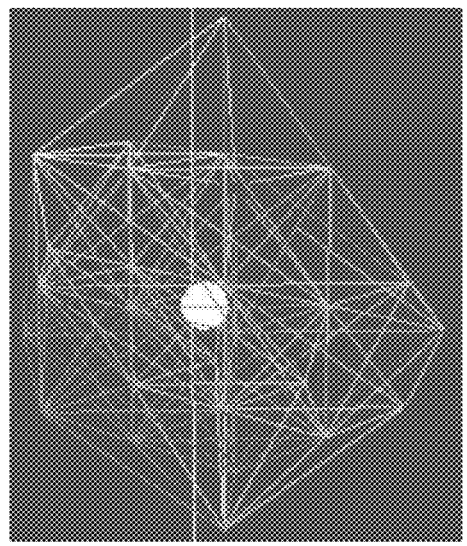

FIG. 7 shows a schematic illustration of MSD connection.

Figure 1:
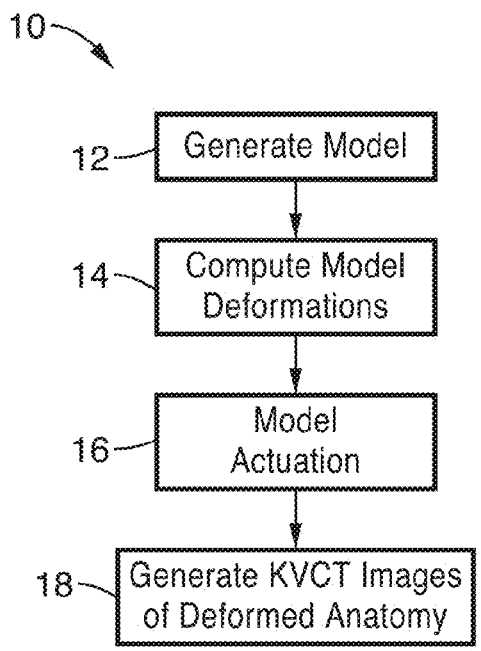
FIG. 1 shows a high level flow diagram for generating ground-truth data for validating deformable image registration (DIR) for head and neck anatomy in accordance with the present description.
Figure 8:
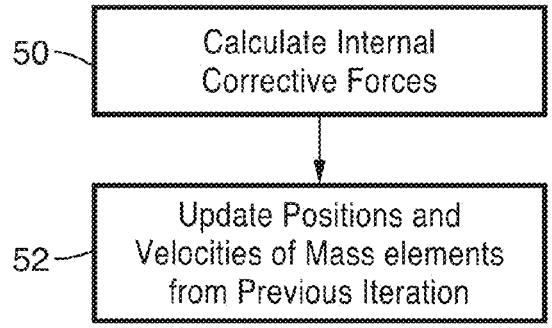

FIG. 8 shows a flow diagram of the model deformation step of FIG. 1.

FIG. 9 shows a detailed flow diagram of posture and physiological change simulation step of FIG. 1.

FIG. 10 shows a detailed flow diagram of the step of generating kVCT images representing the deformed anatomy in accordance with FIG. 1.

FIG. 11 shows a system for developing physics-based high resolution biomechanical head and neck deformable models in accordance with the present description.

Figure 12A:
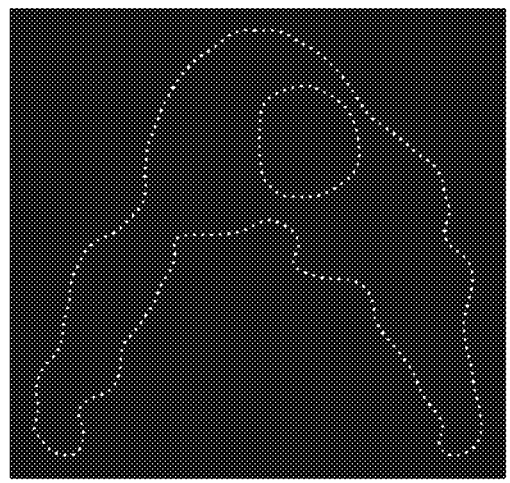

FIG. 12A shows a planar set of disconnected contour points associated with internal and external boundaries.

Figure 12B:
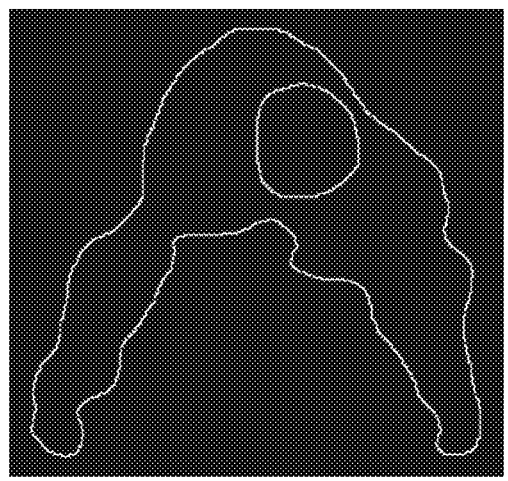

FIG. 12B shows the connected contour boundary generated from planar contour points.

Figure 12C:

FIG. 12C shows the final structure volume with voxels associated with the structure represented in white colored pixels.

Figure 13A:
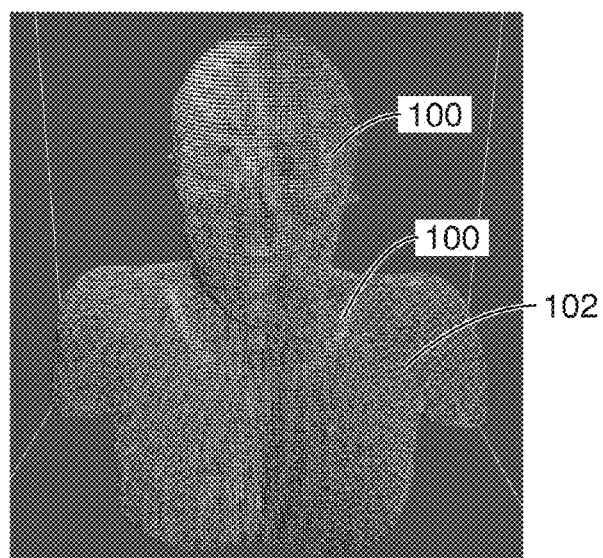
Figure 13B:
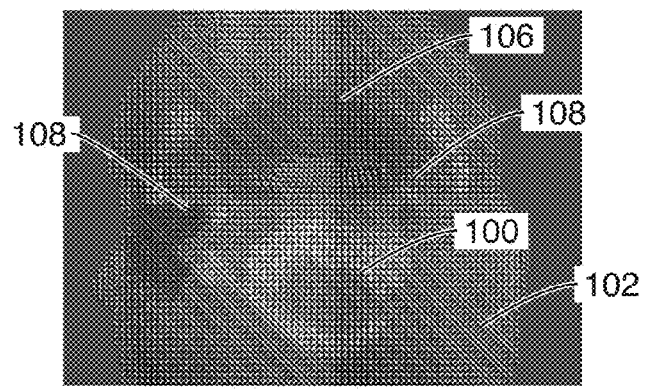
Figure 13C:
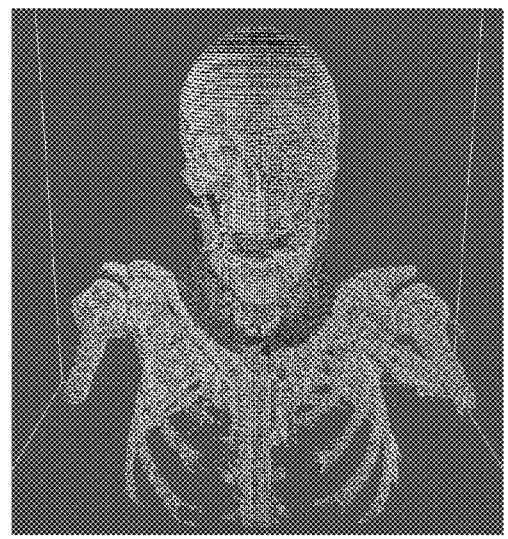

FIG. 13A through FIG. 13C illustrate the head and neck model developed from the reference kVCT. The model in its rest position is shown with the entire anatomy Id shown in FIG. 13A. FIG. 13B shows a 2D slice of the neck region showing the PTV the surrounding soft tissue and the rigid bone structure. FIG. 13C shows the critical contoured structures along with the skeletal anatomy.

Figure 14A:
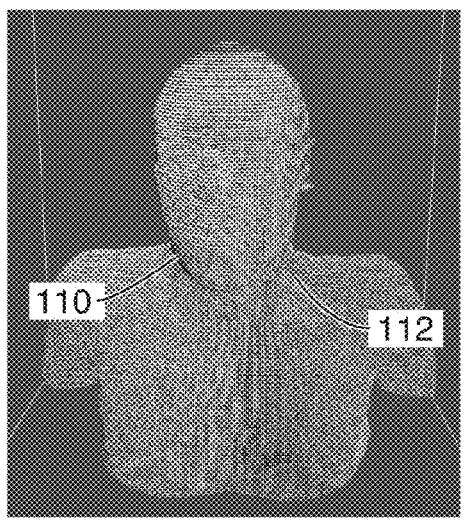
Figure 14B:
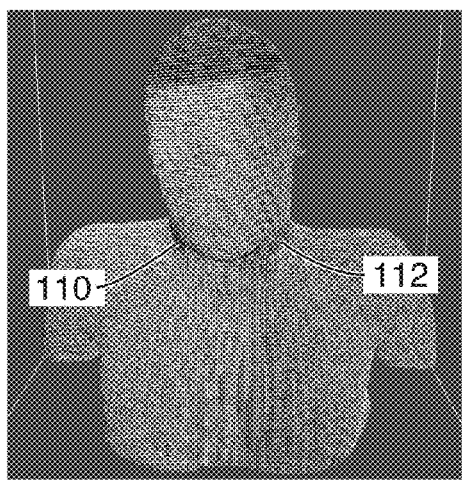
Figure 14C:
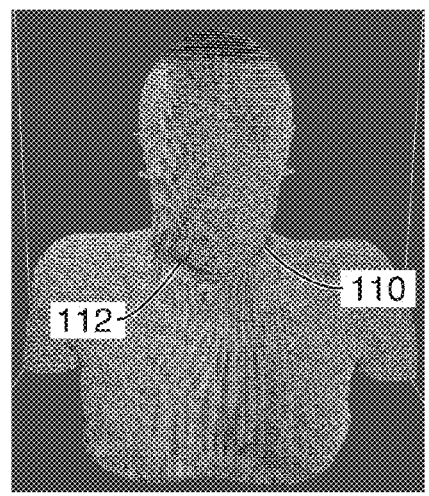

FIG. 14A through FIG. 14C show the biomechanical deformation caused by skull and neck discs rotation along the caudal-cranial axis. FIG. 14A shows the model before the deformation and FIG. 14B and FIG. 14C demonstrate two different neck rotations.

Figure 15A:
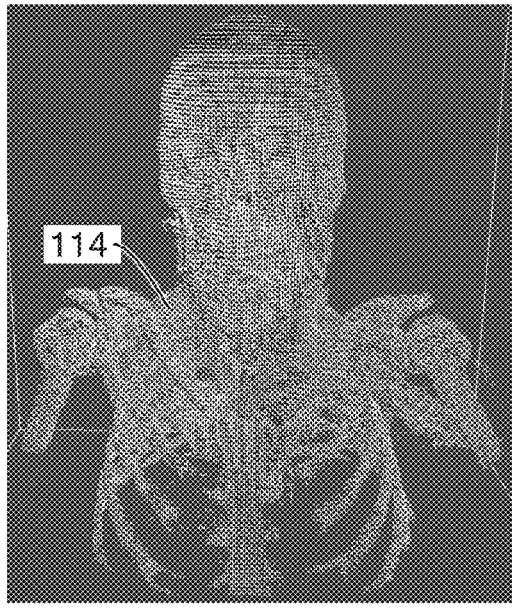
Figure 15B:
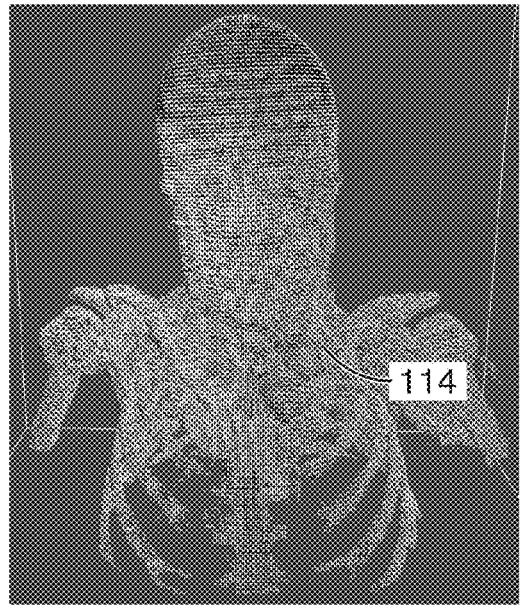
Figure 15C:
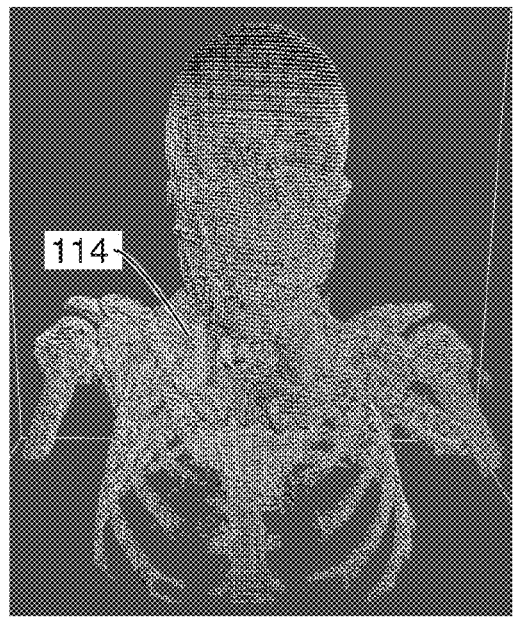

FIG. 15A through FIG. 15C show three examples of the deformation associated with head and neck posture changes, illustrating deformation of the biomechanical model including of the head and neck skeletal structure and PTV, parotid glands and neck muscles. The model before the deformation is shown in FIG. 15A. Two different head and neck rotations are demonstrated in FIG. 15B and FIG. 15C.

Figure 16A:
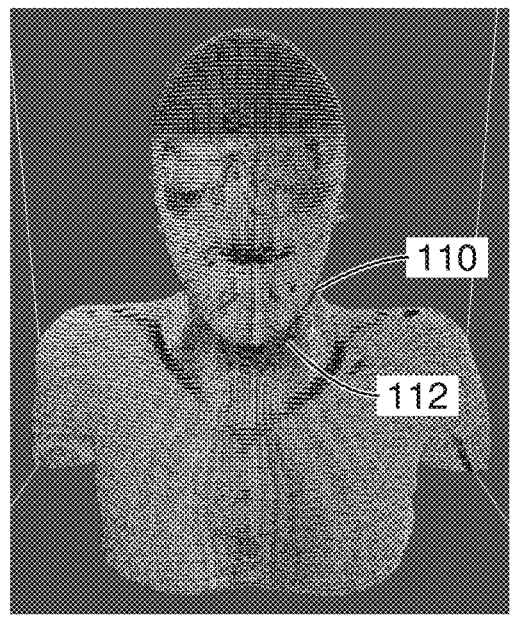
Figure 16B:
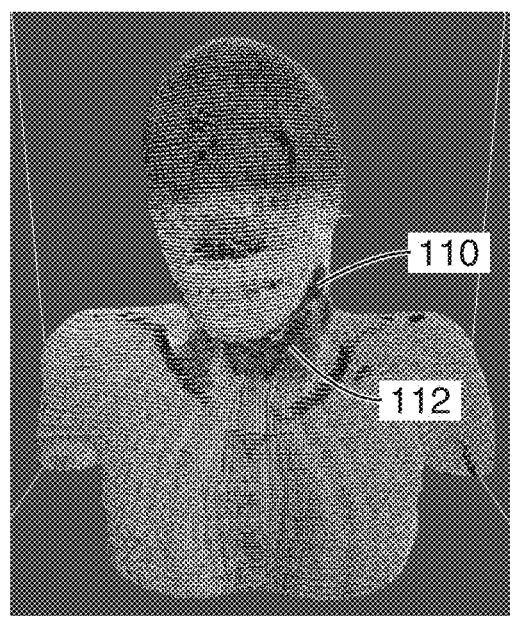

FIG. 16A and FIG. 16B show model results for simulating physiological regression using the reference biomechanical model (shown in FIG. 13A) with only radiation sensitive structures in the head and neck region. The model before the posture change is shown in FIG. 16A. A different head and neck posture is demonstrated in FIG. 16B.

Figure 17A:
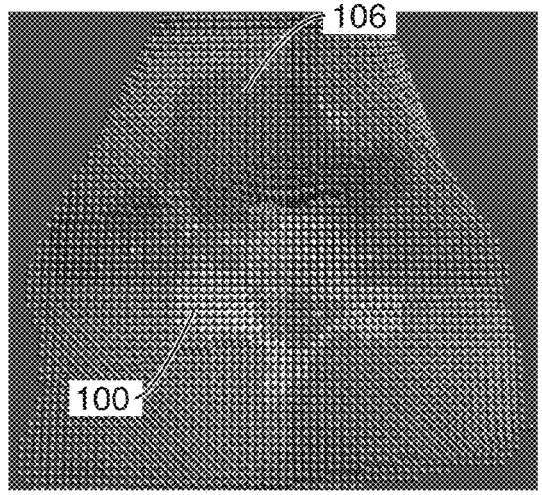
Figure 17B:
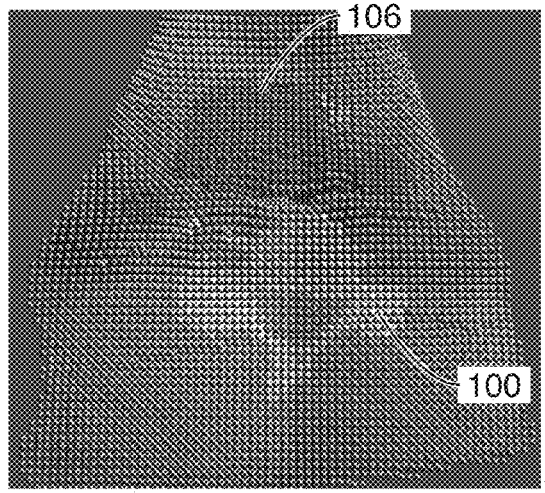
Figure 17C:
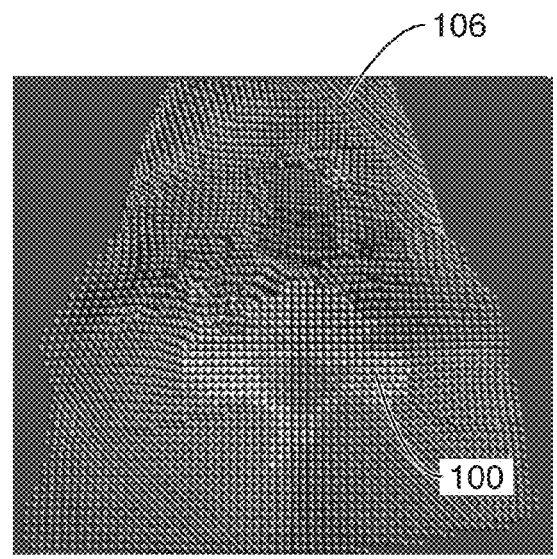

FIG. 17A through FIG. 17C show a slice of the biomechanical model in the neck region with the PTV shaded dark. FIG. 17A shows a 2D snapshot of the model at rest state FIG.

17B and FIG. 17C show its deformed state representing 10% and 40% PTV volume reduction, respectively.

Figure 17D:
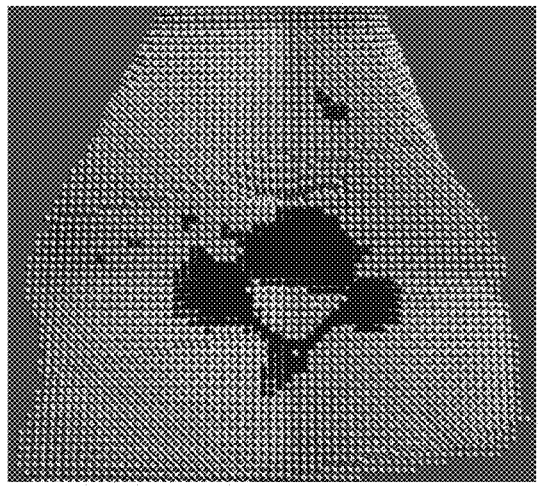
Figure 17E:
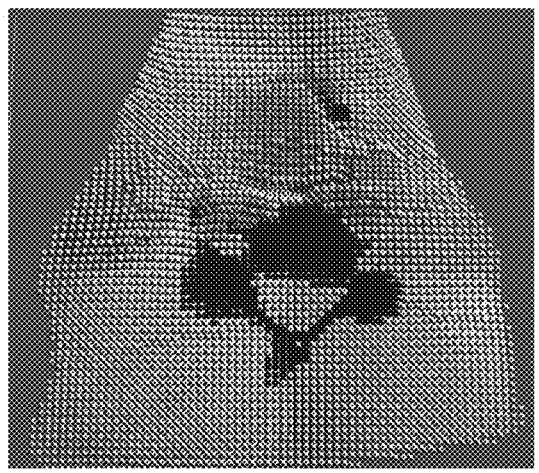
Figure 17F:
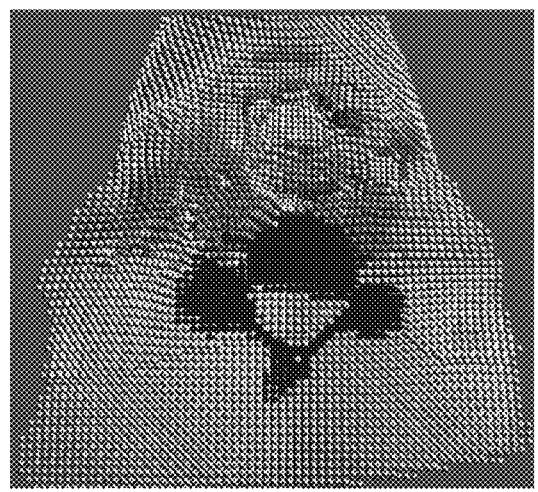

FIG. 17D through FIG. 17F show the corresponding stress in the muscle when compared to the original anatomy state for the three states.

Figure 18A:
Figure 18B:
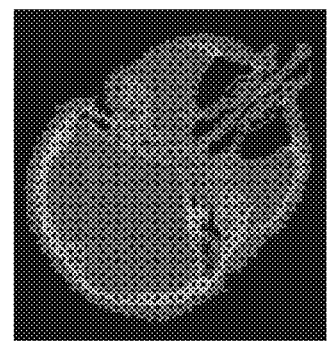
Figure 18C:
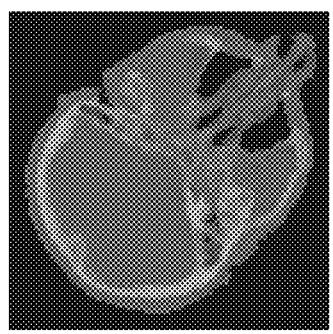
Figure 18D:
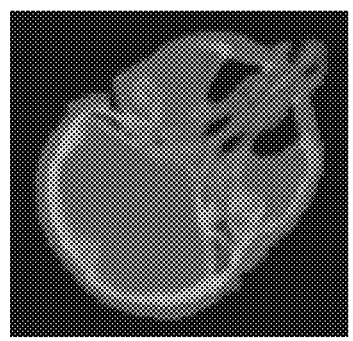

FIG. 18A through FIG. 18D show simulated kVCT image generation and artifact correction, illustrating how the artifacts are compensated for during generation of the simulated kVCT images. FIG. 18A shows an axial slice of the source kVCT used to generate the model. FIG. 18B shows the resultant model generated image after rotating the head by 45°. FIG. 18C shows the holes of FIG. 18B addressed by ray-tracing between model elements, and filling holes with an interpolated intensity. FIG. 18D shows the aliasing of FIG. 18B addressed using a texture based smoothing algorithm to produce the final image.

Figure 19A:
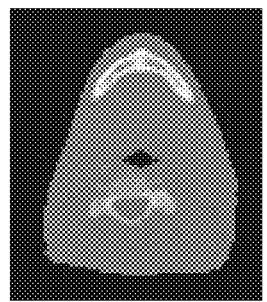
Figure 19B:
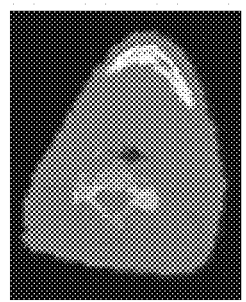
Figure 19C:
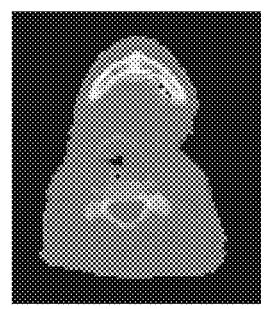
Figure 19D:
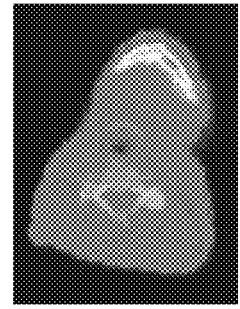

FIG. 19A through FIG. 19D show simulated kVCT images corresponding to different states of deformation and rotation. FIG. 19A shows the KVCT slice at rest state. FIG. 19B shows the state where the neck is rotated by 10 degrees. FIG. 19C shows a KVCT slice representing the same anatomy with the PTV reduced by 30%. FIG. 19D shows the deformation of the model where the skull is rotated by 10 degrees.

Figure 20A:
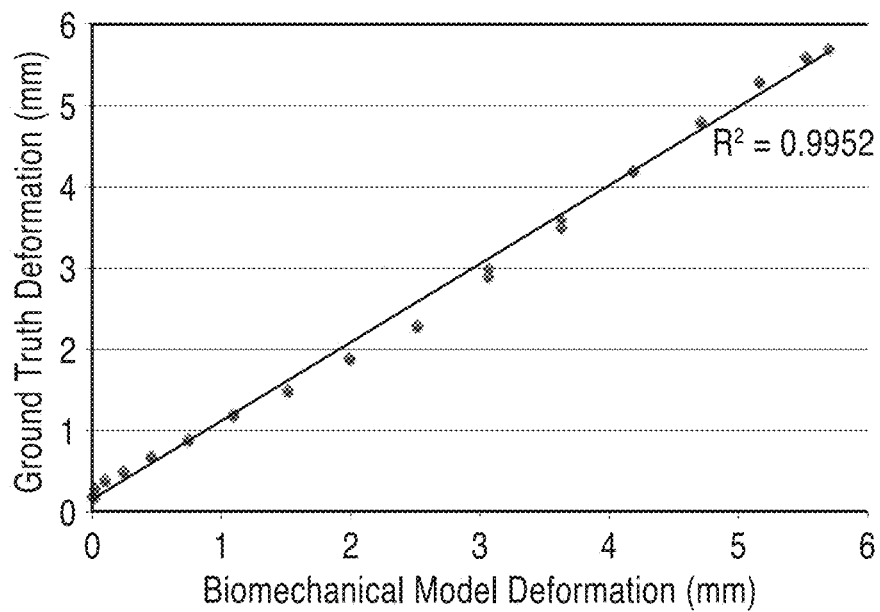
Figure 20B:
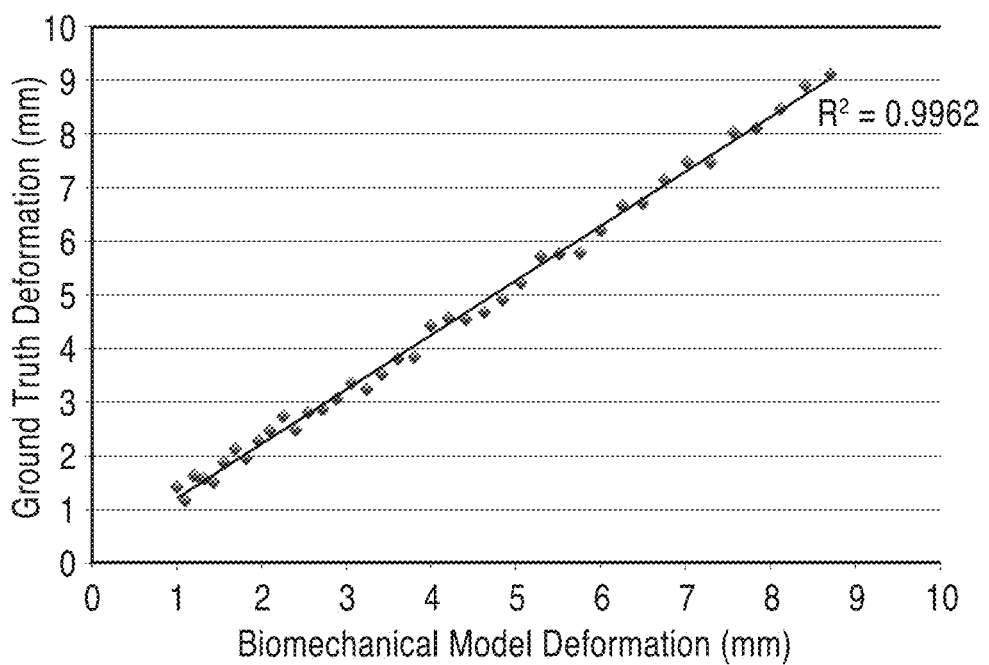

FIG. 20A and FIG. 20B illustrate an elastostatic validation study using local and global force application experiment. FIG. 20A shows the response of a cube of soft tissue to a local load applied in the form of a spherical mass. FIG. 20B shows the response of a cube of soft tissue in response to being compressed by gravity.

Figure 21A:
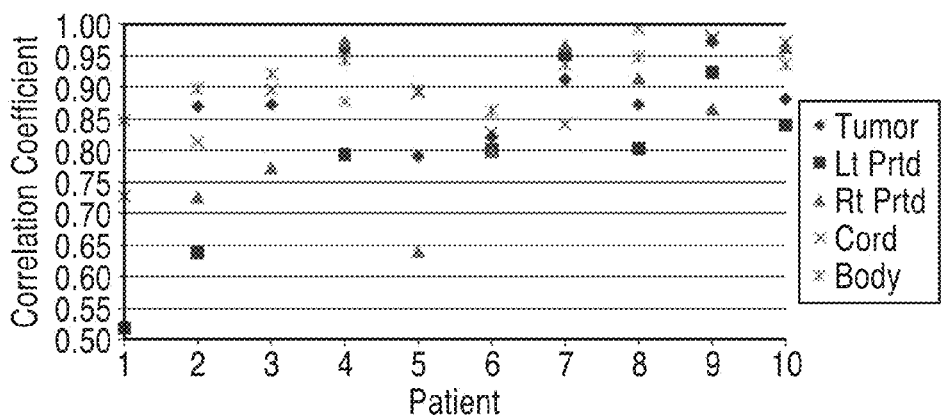
Figure 21B:
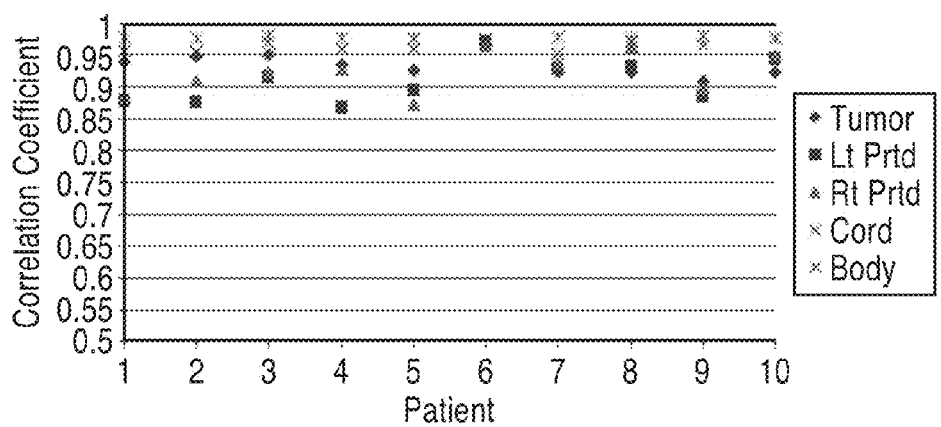
Figure 21C:
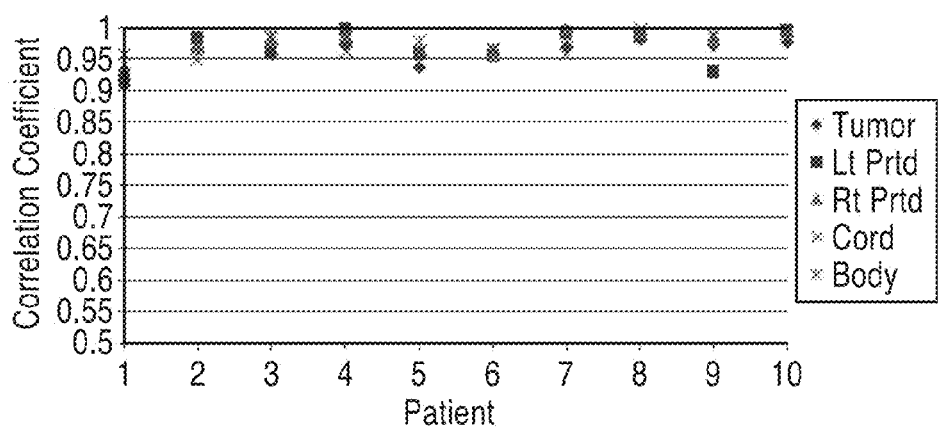

FIG. 21A through FIG. 21C illustrate the correlation of model generated data sets with induced soft tissue deformation from posture changes with clinically observed deformation. FIG. 21A shows the baseline correlation between the planning CT used to generate the biomechanical model and the target CT used as the deformation endpoint. FIG. 21B shows the correlation after applying posture changes to the model to match the weekly CT. FIG. 21C shows the correlation after the inclusion of tumor regression to the model.

Figure 22A:
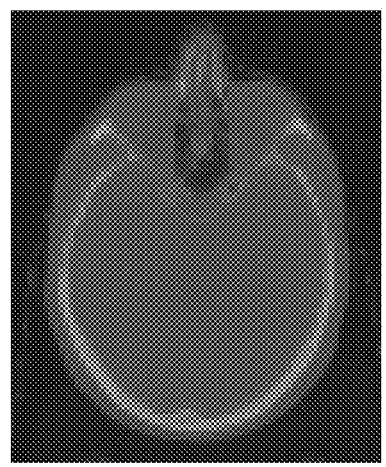
Figure 22B:
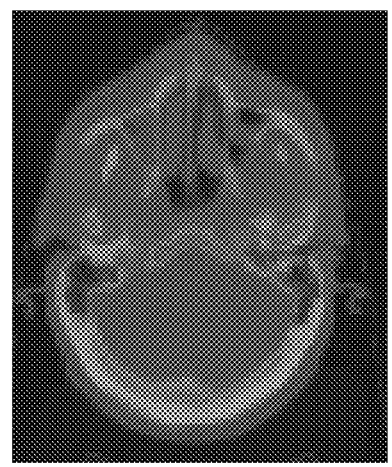
Figure 22C:
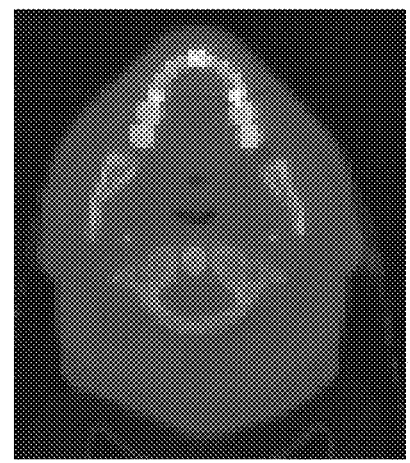

FIG. 22A through FIG. 22C illustrate model generated kVCT images overlaid on weekly kVCT images at three axial levels. Light areas show good agreement between the model generated images and the weekly CT images. Darker tinted areas show a disagreement where one image had a higher intensity.

DETAILED DESCRIPTION

FIG. 1 through FIG. 22C are directed to systems and methods for developing physics-based high resolution biomechanical head and neck deformable models, which are instrumental for applications ranging from computer animations to medical imaging and simulations.

To construct precise ground-truth data for validating DIR for clinically realistic deformations where the motion of each voxel is known, the biomechanical models ideally satisfy the following: (a) one-to-one model correspondence with the reference anatomy, i.e., for every voxel in the reference anatomy, the model includes a model element (e.g. a node with an assigned mass and elasticity), and vice versa, (b) simulation of both posture as well as physiological changes, and (c) model validation to ensure clinical relevance.

In order to address the high computational demands of the systems and methods of the present description, the algorithms embodiment in said systems and methods are ideally employed as a Graphics Processing Unit (GPU) based computational framework.

FIG. 1 shows a high-level flow diagram of a method 10 for generating ground-truth data for validating deformable image registration (DIR) for head and neck anatomy. First, a model is generated at step 12. Model deformations are computed at step 14. The model is then actuated at step 16. Finally, kVCT images of the deformed anatomy are generated at step 18.

FIG. 2 shows a schematic flow diagram for the model generating step 12 shown in the flow diagram of FIG. 1.

First, at step 22, image data (e.g. kVCT images) are acquired. Images for the experiments of the present description (provided in further detail below) were acquired as part of an IRB-approved prospective adaptive radiotherapy protocol at M.D. Anderson Cancer Center Orlando. The planning kVCTs, as well as the repeated weekly kVCTs for all the patients, were acquired using a Philips Brilliance CT system (Philips Medical Systems, Best, the Netherlands) or a Siemens Biograph 64 PET/CT system (Siemens AG, Munich, Germany) with 1×1×3 mm$^3$ reconstructed resolution. Soft tissue and rigid structures were manually contoured in each of the datasets using a commercial contouring tool (e.g. MimVista Inc., Cleveland, Ohio).

Figure 3:
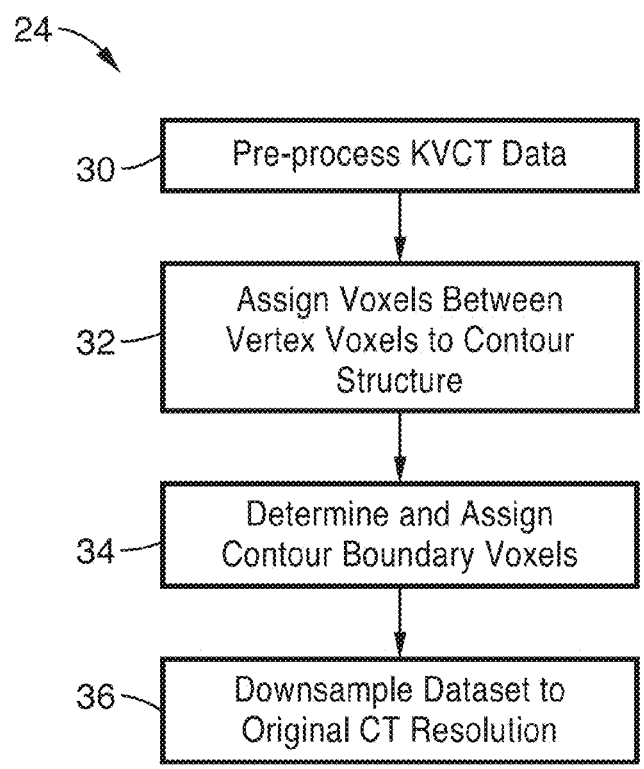
FIG. 3 shows a detailed flow diagram for the structured volume generation step of FIG. 2.

At step 24, a structured volume algorithm was developed to assign the voxels based on the contour vertices. The contours represent the structure outlines and are transmitted as an ordered series of contour vertices. In a preferred embodiment, method 10 ideally assigns of each voxel to a single structure via the structured volume generation (also referred to as "contour-filling algorithm") of step 24, which is provided in further detail in FIG. 3. FIG. 4A through FIG. 4C further show schematic diagrams illustrating the contour-filling algorithm 24 in accordance with the present description. The algorithm was as follows:

Referring to FIG. 3, the structured volume algorithm 24 first pre-processes the kVCT data at step 30 by creating a secondary voxel grid at 5× in-plane resolution of the CT scan, and assigning the secondary grid voxels that overlapped the contour vertices to the contour structures, which is defined as the 3D voxelized volume described by the contour points. These voxels are termed "vertex voxels." FIG. 4A depicts a 2D slice representation with two contour boundary points (vertex voxels) S and T.

Next at step 32, voxels that lay between consecutive vertex voxels are assigned to the contour structure (e.g. using Bresenham's algorithm) with the additional constraint that neighboring assigned voxel pairs share either the same x or y value. FIG. 4B illustrates the voxel assignments connecting the boundary points using the Bresenham's line generating algorithm.

At step 34 of FIG. 3, the voxels inside the contour boundary voxels S and T were determined and assigned using a GPU-based algorithm. FIG. 4C illustrates the additional voxel assignments to the connected boundary points using the additional constraint. The ordinal rays passing through the contour without intersecting the boundary points are illustrated in FIG. 4B, while the ordinal rays passing through the contour intersecting the boundary points are illustrated in FIG. 4C. This process was repeated for all vertex voxels, leading to a series of assigned voxels that formed a closed boundary. The assigned voxels are termed "boundary voxels."

The GPU-based algorithm of step 34 operates according to steps (a) through e below:

(a) The secondary voxel grid is imported to 3D texture memory.

(b) For each unassigned voxel, an accumulator value is created and initialized to 0.

(c) Parallel rays along the eight cardinal and ordinal directions are passed through each axial plane of the 3D texture.

(d) Each ray samples every voxel it intersects and updates the voxel's accumulator value. When the ray encounters its first boundary voxel, it adds 1 or 2 to every subsequent unassigned voxel's accumulator it intersects for ordinal or cardinal rays, respectively. The process continues until the ray encounters a second boundary voxel (of any contour). At that point, it stops adding to the accumulator. As the ray meets subsequent boundary voxels, the accumulation process repeats until the ray exits the volume.

(e) Once all the rays are traversed, the accumulator dataset is analyzed, and voxels with an accumulator value of 11 or 12 (the maximum), are considered part of the contoured structure.

FIG. 4B and FIG. 4C exhibit the ray intersection with the dataset, and illustrate the requirement of the modification to Bresenham's algorithm. While the cardinal rays pass through the boundary voxel initiating the accumulation process, the ordinal rays do not intersect with the boundary, and may lead to errors. FIG. 4C depicts the ordinal rays passing through the contoured boundary, illustrating the utility of the structured volume generation algorithm 24 presented above.

Finally, at step 36 the dataset is down-sampled to the original CT resolution, and voxels with greater than 50% of their volume within the contour are considered to be entirely within the contour.

Referring back to FIG. 2, the next step in the biomechanical model generation process 12 is to initialize the biomechanical model's anatomy via mass element generation step 28. The biomechanical model is defined as a series of connected mass elements with associated mass-spring damping (MSD) connections in a deformation space where it may be deformed and manipulated. Mass elements are generated at the center of each voxel within the structured volume. For an accurate mass element assignment to specific structures, the following two constraints are implemented:

(a) each contour set includes a body contour that covers the entire head and neck anatomy, ensuring that no mass element inside the body was excluded from being assigned to a contour structure; and (b) no two contour structures overlap with each other, ensuring that no ambiguity exists in the mass element assignment process.

Each of the mass elements are then associated with a Young's modulus and a Poisson's ratio based on the anatomy as previously tabulated or available for parotid glands and other structures. In addition, the damping coefficient for each of the mass elements is set to 0.43.

After mass element generation, an MSD connection initialization algorithm is applied at step 28, which connects the mass elements with each other using a spring damper formulation to ensure that the mass elements deform in a physically realistic manner.

MSD connection initialization algorithm 28 is further detailed in the flow diagram of FIG. 5, and is schematically illustrated in the diagrams of FIG. 6 and FIG. 7. Referring to FIG. 5, the deformation space is first sub-divided into a 3D uniform cell grid at step 40, and each mass element was assigned a hash value (or an identification value) at step 42 based on the cell that contained it (cell ID, as shown in FIG. 6).

Next, at step 44, mass elements are then sorted by their hash value using a GPU-based fast radix algorithm. Once sorted, a local neighborhood search is then performed at step 46 in a parallelized manner around each mass element (hereafter referred to as the search element), to find nearby mass elements. For example, in one exemplary embodiment, a 5×5×5 cell neighborhood may be searched to establish connections as a 3×3×3 cube, creating 26 "springs" per element.

When a nearby mass element is within a threshold distance (determined by the voxel size of the input CT) from the search element, an MSD connection is established at step 48, and the nearby mass element becomes a connected element for the given search element, as illustrated in FIG. 7.

The steps in MSD connection step 48 may be performed as follows: first, an array in the GPU memory is initialized to hold mass element identifiers for the connected elements of each search element. A second array is initialized in the GPU memory to hold rest state orientations for each of the connections, where the rest state orientation is defined as the vector from the search element to the connected element. At the end of this step, the biomechanical model step 12 is complete.

Referring back to FIG. 1, with the model complete, the method next computes model deformations at step 14. The head and neck deformations are defined to be actuated by user-defined rigid transformations of skeletal structures. While the skeletal structures undergo rigid transformations, the muscles and the soft tissues in the head and neck region undergo elastic deformations governed by internal correctives forces. Referring to the detailed flow diagram of model deformation step 14 in FIG. 8, the internal corrective forces on each mass element are calculated at step 50 as a summation of tensile spring force, shear spring force, and a dashpot damping force. At rest state, the elastic internal corrective forces are set to 0. When deformed (as discussed in further detail below), the model's mass elements are relocated to new positions inside the deformation space at step 52, which causes the internal corrective forces to be non-zero.

The calculation of the internal corrective forces at step 50 begins by computing the tensile spring force, $\vec{f}_{Y,ab}$, between mass elements a and b via Eq. 1:

$$\vec{f}_{Y,b} = \frac{Y_a + Y_b}{2}\left(\frac{|\vec{p}_{ab}| - |\vec{l}_{ab}|}{|\vec{l}_{ab}|}\right)\frac{\vec{p}_{ab}}{|\vec{p}_{ab}|}, \quad \text{Eq. 1}$$

where $Y_a$ and $Y_b$ are the elastic moduli for mass elements a and b, respectively, $\vec{l}_{ab}$ is the rest length orientation for MSD connection between mass elements a and b, and $\vec{p}_{ab}$ is the projection according to Eq. 2:

$$\vec{p}_{ab} = \frac{\vec{l}_{ab}}{|\vec{l}_{ab}|}\left(\frac{\vec{l}_{ab} \cdot \vec{l}'_{ab}}{|\vec{l}_{ab}|}\right), \quad \text{Eq. 2}$$

where $\vec{l}_{ab}'$ is the vector from mass element a to mass element b in the deformed state.

The shear spring force, $\vec{f}_{S,ab}$, on mass element a due to mass element b applied along a rejection vector, $\vec{r}_{ab}$, is calculated to Eq. 3:

$$\vec{f}_{S,b} = -\frac{S_a + S_b}{2}\left(\frac{\vec{r}_{ab}}{|\vec{l}_{ab}|}\right), \quad \text{Eq. 3}$$

where $S_a$ and $S_b$ are the shear moduli for mass elements a and b, respectively, and $$\vec{r}_{ab} = \vec{l}_{ab}' - \vec{p}_{ab} \quad \text{Eq. 4}$$

The dashpot damping force, $\vec{f}_{v,ab}$ is calculated from the relative velocities of the mass elements, $\vec{v}_a$ and $\vec{v}_b$, and a local damping factor $\mu_{ab}$ according to Eq. 5:

$$\vec{f}_{v,b} = \mu_{ab}(\vec{v}_b - \vec{v}_a) \quad \text{Eq. 5}$$

The internal corrective force, $\vec{f}_a$, on mass element a is then computed by summing over all its spring connections via Eq. 6:

$$\vec{f}_a = \sum_b (\vec{f}_{Y,b} + \vec{f}_{S,b} + \vec{f}_{v,b}). \quad \text{Eq. 6}$$

Once the internal forces are computed, the new positions, $\vec{x}_a^{n+1}$, and velocities, $\vec{v}_a^{n+1}$, of the mass elements are updated at step 52 from the values ($\vec{x}_a^n$, $\vec{v}_a^n$) at the previous iteration n, using Implicit (Backward) Euler integration:

$$\vec{v}_a^{n+1} = \vec{v}_a^n + \left(\frac{\vec{f}_a}{m_a} + \vec{g}\right)\delta, \quad \text{Eq. 7}$$

$$\vec{x}_a^{n+1} = \vec{x}_a^n + \vec{v}_a^{n+1}\delta, \quad \text{Eq. 8}$$

where δ is the time step between iterations, $m_a$ is the mass of mass element a, and $\vec{g}$ is acceleration due to gravity.

Referring back to FIG. 1, the next step in method 10 is actuating the biomechanical head and neck model to represent posture and physiological changes at step 16.

FIG. 9 shows a detailed flow diagram of posture and physiological change simulation step 16. Simulating posture changes are conducted using a three-step model actuation procedure. In the first step 60, the 3D skeletal anatomy is transformed using a graphical user-interface that controls the individual contoured skeletal structures such as the skull, mandible, and cervical vertebrae.

At steps 62 and 64, the muscle and the soft tissues are then deformed by applying the soft tissue corrective forces as calculated in step 14 above. During this transformation, the skeletal rotations are constrained at any step to be not more than one degree about a single axis to ensure that the soft tissue deformations occur in small steps. From a computational perspective, such small soft tissue deformations avoid instabilities that may arise from time integration computations. In step 62, each of the contoured muscle structures are deformed with the skeletal and other soft-tissue positions as rigid-body constraints. Similarly at step 64, the remaining soft tissue deformations outside any contoured structures were computed with the muscle deformation and skeletal transformations being taken as rigid-body constraints. The deformation process is repeated until all the soft tissue structures reach equilibrium deformations.

Physiological changes are incorporated on a 3D structured volume basis using a two-step iterative approach. For illustration purposes, a scenario is used wherein a planning target volume (PTV) undergoes regression with all the other structure volumes undergoing normal elastic deformations. In step 66, the PTV regression is computed with its surrounding structures providing a rigid-body constraint. For a given change in the PTV volume, the surface area of the PTV volume is reduced in a physically accurate manner by decreasing the rest length of each connection inside the PTV. It was performed as follows: Before a volume change was initiated inside the PTV, its mass elements were clustered to form a set of cuboids. The volume of the set of cuboids was summed to represent the PTV volume.

Using the initial cuboid volume V; and the volume change v; for a cuboid i, the change in rest length $a_i$ was computed using Eq. 9:

$$(l+a_i)*(w+a_i)*(h+a_i) = V_i + v_i, \quad \text{Eq. 9}$$

where l, w, and h are the length, width and height of each cuboid. From a physiological perspective, the rest length change $a_i$ demonstrates the loss or gain in volume. In order to maintain a stable deformation, the rest length change is constrained to be not greater than 2 mm per iteration. The change in the rest length leads to internal elastic corrective forces that subsequently deform the PTV to reflect the volume regression.

At step 68, the reduced PTV is considered as a rigid body constraint and the remaining soft tissue anatomy surrounding the PTV is deformed as previously explained above. The two-step iterative process continues until the entire anatomy deformation converges.

Referring back to FIG. 1, the final step in method 10 is step 18 of generating kVCT Images representing the deformed anatomy.

Due to the deformed anatomy, there is not a one-to-one correspondence between mass elements and image voxels. This leads to the following issues: (a) gap artifacts where voxels enclosed no mass elements but had a transiting MSD connections, (b) hole artifacts, and (c) aliasing artifacts arising from skeletal head and neck rotations. These three issues were addressed via step 18 as illustrated in further detail in FIG. 10.

First, at step 70, a new data volume is initialized that represents the synthetic CT image of the biomechanical model in the deformed state. The data volume dimensions and resolutions are set to be the same as that of the reference kVCT image.

Next, at step 72, for every mass element in the biomechanical model, the current position is converted from the deformation space into a voxel address in the new data volume.

At step 74, each of the new voxels is assigned the Hounsfield intensity (HU) originally associated with the enclosed mass element, or the average HU of multiple enclosed elements.

At step 76, the process addresses any hole/gap artifacts via sub-steps (a) through (d) as follows:

(a) Ray-traces are defined between every mass element along MSD connections, with interval sampling equal to half of the MSD connection's rest length.

(b) For every mid-MSD sampled position in the deformation space, the corresponding position in the new data volume is evaluated to see if it was in an empty voxel.

(c) When the mid-MSD sampled position is in an empty voxel, the HU value is interpolated from the two mass elements connected by the MSD connection with the interpolation weighted by their relative distances from the sample position.

(d) If one of the mass elements is skeletal anatomy, its corresponding weight is set to 0 to ensure the new data volume maintains the same rigid skeletal structure shape as that of the reference kVCT.

Finally, at step 78 a GPU-based linear intensity smoothing routine is applied to reduce the aliasing artifacts that occurred during head rotation, The smoothing routine 78 works as follows:

(a) The new data volume holding the synthetic CT anatomy is loaded into the GPU's texture memory, and is sampled at twice its current resolution.

(b) The tri-linear intensity smoothing is then applied on the up-sampled data to remove the aliasing artifacts. The intrinsic interpolation removes the artifacts from the feature edges.

(c) This interpolated image is then down-sampled to the original dimensions to produce the final synthetic CT.

FIG. 11 shows a system 80 for developing physics-based high resolution biomechanical head and neck deformable models in accordance with the present description. System 80 includes a computing device 84 (e.g. computer, server, etc.) that inputs kVCT image data 82 and outputs kVCT images 94 of deformed anatomy. The system 80 includes application software 86 that preferably includes instructions incorporating the method 10, and graphic user interface for operating the method 10 illustrated in FIG. 1 through FIG. 10 above. Application software 86 is stored in memory 88 and preferably configured to be executable on GPU processor 90 for acting on the acquired data 82 to generate output 94. However, it is appreciated that one or more functions of application software 86 may be performed on CPU 92, is necessary or desired. Appendix A contains an example of code in c and C++ that implements one or more features of application software 86 according to an embodiment of the technology.

EXAMPLE

The model development systems and methods of the present description were applied to a reference head and neck kVCT anatomy and its associated contoured structures to test for efficacy. The structure volume generation algorithm 24 described above was applied to precisely associate the head and neck voxels to their corresponding contoured structures.

FIG. 12A shows a planar set of disconnected contour points associated with internal and external boundaries. FIG. 12B shows the connected contour boundary generated from the planar contour points. The algorithm was able to form nested and distinct boundaries. FIG. 12C shows the final structure volume with voxels associated with the structure represented in white colored pixels. It can also be seen that the structure volume generation algorithm accurately distinguished the structures inside the inner-most circular boundary to not belong to the contoured structure volume and not associate them with the structure.

FIG. 13A through FIG. 13C illustrate the head and neck model developed from the reference kVCT. FIG. 13A shows the rest state of the biomechanical model. The rigid skeletal anatomy is shown in white mass elements 100 while the deformable soft tissues are shown in darker mass elements 102. The volumetric nature of the biomechanical model is shown in FIG. 13B using a 2D slice of the 3D deformable model anatomy that included the darker contour filled PTV elements 106 and the bone anatomy 100. The parotid glands on either side of the PTV 106 are also shown in mass elements 108. The structure volume generation also enables selecting structures undergoing deformation and coupling them with the bone anatomy. FIG. 13C shows the critical contoured structures along with the skeletal anatomy. Each of the contoured structures is shown using a distinct shaded representation. It is appreciated that while the images shown in FIG. 13A through FIG. 13C are illustrated in grayscale, that actual output is preferably shown in various color representations for clarity.

FIG. 14A through FIG. 14C show the biomechanical deformation caused by skull and neck discs rotation along the caudal-cranial axis. The local strain observed in the anatomy was color-coded to represent soft tissue contraction 110 and stretch 112 as quantified in Table 1. The soft tissue regions that underwent neither a contraction nor a stretch were colored green. Deformation differences showed the subtle soft tissue and muscle deformations caused by changes in the patient posture during radiotherapy treatment. They also showed the model's fidelity in representing the 3D deformations that a head and neck anatomy undergoes during different postures. Nevertheless, a visual evaluation of the deformations observed for each of the postures also suggested the qualitative accuracy of the observed deformations.

Three examples of the deformation associated with head and neck posture changes are presented in FIG. 15A through FIG. 15C, which show the deformation of a biomechanical model including of the head and neck skeletal structure and PTV, parotid glands and neck muscles (see FIG. 13C). Other muscle structures were excluded for this simulation. The biomechanical deformation of the critical structures 114, in this case, was caused by skull and cervical vertebrae rotation along the body axis. The strains associated with each of the mass elements are color coded as previously discussed in Table 1. The strains signified a local stretch and contraction that occurred during such skull rotations representing posture changes. The differences in the deformation also showed the muscle deformations caused by changes in the patient posture.

The model results for simulating physiological regression using the reference biomechanical model (shown in FIG. 13A) are shown in FIG. 16A through FIG. 16C. The PTV was shrunk by 30% to simulate tumor regression. The local distribution of the regression is shown in FIG. 16A, illustrating the local variations in the tissue expansion and contraction. FIG. 16B shows the head and neck deformation when the head and neck skeletal structure was rotated by angle of 10 degrees, both local tissue stretching 112 and tissue compression 110 can be seen during head and neck rotation with simulated PTV regression.

FIG. 17A through FIG. 17C show a slice of the biomechanical model in the neck region with the PTV shaded dark. FIG. 17D through FIG. 17E show the corresponding stress in the muscle when compared to the original anatomy state. FIG. 17B shows the internal model changes caused by simulating a PTV shrinkage of 10%. The corresponding deformation strain is shown in FIG. 17E. Similarly, FIG. 17C shows the internal model changes caused by simulating a PTV shrinkage of 30% with the corresponding deformation strain shown in FIG. 17F. A significant amount of deformation outside the PTV can be observed for each of the cases signifying the role of biomechanical head and neck model. The local distribution of the regression demonstrated the local variations in the tissue expansion and contraction for known PTV regression.

FIG. 18A through FIG. 18D illustrate how the artifacts are compensated for during generation of the simulated kVCT images. The source CT used to generate the model is shown in FIG. 18A. After a 45 degree rotation, the hole artifacts are abundant in FIG. 18B. FIG. 18C shows an image after ray-tracing is used to fill the holes, but jagged edges are still apparent. The texture based smoothing algorithm is applied in FIG. 18D to produce the final simulated kVCT data set.

Simulated kVCT images corresponding to different states of deformation and rotation are as shown in FIG. 19A through FIG. 19D. Specifically, FIG. 19A shows the 2D slice generated from the model at rest state. The corresponding slice with 30% PTV regression is as shown in FIG. 19C. The underlying non-rigid deformation of the anatomy during the neck rotation is evident in FIG. 19B with no PTV regression and FIG. 19D with 30% PTV regression. The differences in the deformations stemmed from changes in the PTV region. Such deformations can only be simulated using a high-resolution physics-based deformation model, which is a key contribution of the paper.

In order to validate the numerical accuracy of the biomechanical model, first the general deformation mechanics were tested by comparing the soft tissue response to local global loads with analytic ground truth calculations. Next, the head and neck models were validated by inducing clinical posture changes in the bony anatomy and comparing the soft tissue deformations induced in the model with the deformations recorded in the clinical data. Lastly, the effect of tumor regression was validated by applying a clinically observed deformation to the tumor and comparing the soft tissue deformations induced in the model with the clinical data.

The local load simulation examined the model deformations by applying a known amount of force using a 5 cm radius rigid sphere onto a 10×10×10 cm³ cubic piece of tissue and determining the subsequent deformation using the model. The ground truth deformation was computed using a classical Euler beam theory, which is a simplified method of calculating deflection due to a load using the linear theory of elasticity. The two deformations were compared along the row of soft tissue voxels that lay on the cube surface and intersected the contact point between the sphere and the cube. The deformation computed using the proposed system matched the ground truth with a $R^2$ fit value of >0.98, as shown in FIG. 20A, which shows a numerical comparison of the elastostatic displacement for a column of voxels plotted against ground truth computed using a Green's function solution.

The global load simulation dealt with scenarios where the entire soft tissue structure was applied with an uniform load (e.g. gravity). In the first of two scenarios, the top layer of the soft tissue was anchored and a gravitational force was applied. The resulting deformation was compared with a previously provided numerical solution. In the second scenario, the direction of gravity was reversed, which led to tissue compression. The model predicted deformation matched well with the ground truth with an $R^2$>0.98 for both scenarios, the results of the hanging mass are shown in FIG. 20B.

For the purpose of producing ground truth data to be used for DIR validation in head and neck radiotherapy, the biomechanical model needed to be able to reliably reproduce the type of deformations typically seen in the clinic. To validate the model's ability to do this, 10 patients were selected that had weekly kVCT scans over the course of their radiotherapy treatment. An image registration was performed between the initial planning kVCT and a kVCT acquired during the final week of the patient's treatment to obtain the changes in the skeletal positions in the head and neck region. A biomechanical model was assembled from the initial planning CT, and the deformation vectors obtained from the DIR for the skeletal anatomy were applied to the model's skeletal anatomy. This forced the model into the posture of the final week's kVCT, while allowing the soft tissue to deform in response to the changes in skeletal anatomy. An image-based analysis was then performed comparing the planning CT, the final weekly kVCT, and the model-generated kVCT equivalent. The Pearson product-moment correlation coefficient, was used as the image metric for this analysis. Eq. 10 shows the correlation coefficient, with $X_i$ and $Y_i$ representing a voxel intensity of the ground-truth (final week's kVCT) and test data (model-generated kVCT) sets, while X and Y represent the mean intensity of the corresponding data sets.

$$r = \frac{\sum_{i=1}^{n}(X_i - \overline{X})(Y_i - \overline{Y})}{\sqrt{\sum_{i=1}^{n}(X_i - \overline{X})^2 \sum_{i=1}^{n}(Y_i - \overline{Y})^2}} \quad \text{Eq. 10}$$

To establish the baseline correlation, the planning kVCT was first correlated with the final weekly kVCT. Analysis was performed on each contoured structure, as well as the entire head and neck region. The results for the primary tumor target, left and right parotids, the spinal cord, and the body are shown in FIG. 21A for each of the ten patients. The correlation varies greatly from patient to patient, as the standard deviation for the average correlation of a structure approached 20%. For patient 1, the tumor and right parotid had correlations below 0.5.

The correlation between the model generated data set and the final weekly CT is shown in FIG. 21B. The displacement of soft tissue voxels ranged from 9.3 to 24.3 mm, with an average maximum of 15.3±4.9 mm. The correlation increased significantly in all cases. The average correlation of the tumor increased from 0.844±0.136 to 0.934±0.017.

This experiment, however, doesn't allow for physiological changes such as tumor regression. The tumor targets for these patients reduced in volume by an average of 5.1±3.6 mL, with the largest regression in patient 5 at 9.26 mL. The volume changes also induced a shift in the tumor center of mass. The maximum shift was in patient 1 at 15.9 mm, while the average displacement of the center of mass in all 10 patients was 4.44 mm. To validate the model's response to tumor regression, the deformation vectors from the DIR were also applied to the primary tumor target as well as the posture changes to the skeletal anatomy. The correlation between the model generated data with tumor regression and the weekly CT are shown in FIG. 21C. The average correlation coefficient increased from the previous case where only posture changes were introduced. The correlation of the primary tumor target increased to 0.960±0.022.

FIG. 22A through FIG. 22C illustrate model generated kVCT images overlaid on weekly kVCT images at three axial levels. Light areas show good agreement between the model generated images and the weekly CT images. Darker tinted areas show a disagreement where one image had a higher intensity.

The model was able to very closely reproduce the soft tissue anatomy seen in a spectrum of clinical patients when posture changes were induced. When tumor regression was also set to match the clinical data, the correlation increased even further, such that the lowest correlation of the structures analyzed was still greater than 0.9. This experiment illustrated that the model is capable of simulating physics-based deformations that are very close to clinically seen deformations, and validated the model's ability to ultimately generate ground-truth deformations to be used for DIR validation studies.

DIR plays a pivotal role in the head and neck adaptive radiotherapy but validation of various DIR algorithms has been hampered by the lack of a quantitative high resolution ground truth. In this description a GPU based high-resolution biomechanical head and neck model using kVCT images was shown to overcome this difficulty. The biomechanical model of the present description may be used for generating CT equivalent 3D volumes that simulate posture changes and physiological regression in order to validate image-guided patient positioning approaches, for example DIR accuracy of different registration paradigms. The model can also be generated using other volumetric imaging modalities, such as megavoltage CT (MVCT) and cone beam CT (CBCT). Moreover, with the advent of Magnetic Resonance Imaging for both patient simulation and on-board imaging, the model will be an effective tool for generating deformed MRI images and verifying registration accuracy.

It has been previously established that head and neck anatomy involves a complex musculoskeletal feedback system. The present description specifically focuses on deforming the muscle and soft tissue system based on known skeletal positions and orientations. The model actuation effectively simulates head and neck deformation from patient posture and physiological regression. The model is preferably actuated using a simple graphical user interface that individually controls the skeletal structures in the head and neck region. Such a framework enables modeling of soft tissue and muscle deformations representing posture changes. There are multiple methods for introducing anisotropic volume regression. Two simple implementations for the model presented in this paper are adding multiple contours inside a single anatomy and individually controlling the volume regression of the sub-structures, and heterogeneously manipulating the elastic properties of the spring connections of an element. The present description the provides a unique biomechanical model capable of simulating head and neck physiological changes such as volume regression.

The biomechanical head and neck model detailed above preferably employs a mass-spring approach to deform the head and neck anatomy. While several CPU based mass-spring modeling approaches exist, the model discussed in this paper is unique as it employs a very efficient GPU based approach to deform the head and neck anatomy.

One of the salient features of the biomechanical model is its real-time ability to deform. Using state-of-art graphics processing units, it was observed that the model was able to deform at a rate of 60 deformations per second. While the real-time nature of the model may not have a direct impact on the DIR validation, it is contemplated that it will have a significant impact for on-line adaptive radiotherapy where DIR plays a key role. Recent advancements in image segmentation, registration and online adaptive planning has led to systems that can perform their tasks in real-time. Thus having a biomechanical model guided validation that can match the speed provided by these algorithms will also be instrumental for future developments in adaptive radiotherapy.

Applications for the technology of the systems and methods detailed above include, but are not limited to:

(a) Validating the usage of deformable image registration (DIR) for daily patient positioning is critical for adaptive radiotherapy applications pertaining to head and neck radiotherapy. The present description includes systems and methods for generating ground-truth data for validating DIRs for head and neck anatomy by (i) developing a high-resolution deformable biomechanical head and neck model from a planning CT data, (ii) simulating deformations that represent a range of inter-fraction patient posture changes and physiological regression and (iii) generating subsequent CT images representing the deformed anatomy.

(b) Validating adaptive radiotherapy applications. The model may be configured to simulate changes in the patient anatomy and how the new treatment plan can be developed.

(c) Synthetic images that can mimic on-board imaging for a given patient can be simulated in real-time using the systems and methods of the present description.

(d) Animation applications. The range of applications is quite large and can be used for everything in the domain of commercial movie content, 3D sub-surface lighting etc.

Some key features of the systems and methods of the present description include: (a) a GPU framework for deforming a high resolution biomechanical head and neck model at interactive speeds; (b) a model anatomy with a one-to-one correspondence between a planning CT anatomy such that the model can compute the displacement of every voxel in the CT without employing any interpolation; and (c) a model configured to generate an equivalent CT data set for validating image-based registration algorithms.

Accordingly, the focus of this disclosure is on the biomechanical head and neck model development that can be used for validating DIR algorithms for the head and neck anatomy. The human head-neck musculoskeletal system is highly complex with approximately 57 articular bones and many more muscle actuators. Comprehensive biomechanical modeling and control of the head and neck anatomy is the most principled approach for simulating subtle deformations such as neck rotation movements and physiological changes such as tumor shrinkage and internal organ movements. However, it is appreciated that the systems and methods disclosed herein may be applied to other anatomical regions of the body.

It is appreciated that the skeletal model may also be configured to simulate more physically and physiologically realistic articulation. The biomechanical properties in our model disclosed herein were obtained from the literature, but these properties vary between patients. A technique may also be implemented for estimating patient specific tissue elastic properties by inversing the forward deformation model for known deformations. This provides patient specific head and neck biomechanical models which will be useful for adaptive radiotherapy. While others have used low resolution finite element models to estimate elastic properties, the high resolution model of the present description, with its complex musculoskeletal behavior, provides a more accurate estimation. The GPU based platform described herein enables the complex calculations to be performed in parallel and in a scalable fashion in nearly real-time.

Embodiments of the present technology may be described with reference to flowchart illustrations of methods and systems according to embodiments of the technology, and/or algorithms, formulae, or other computational depictions, which may also be implemented as computer program products. In this regard, each block or step of a flowchart, and combinations of blocks (and/or steps) in a flowchart, algorithm, formula, or computational depiction can be implemented by various means, such as hardware, firmware, and/or software including one or more computer program instructions embodied in computer-readable program code logic. As will be appreciated, any such computer program instructions may be loaded onto a computer, including without limitation a general purpose computer or special purpose computer, or other programmable processing apparatus to produce a machine, such that the computer program instructions which execute on the computer or other programmable processing apparatus create means for implementing the functions specified in the block(s) of the flowchart(s).

Accordingly, blocks of the flowcharts, algorithms, formulae, or computational depictions support combinations of means for performing the specified functions, combinations of steps for performing the specified functions, and computer program instructions, such as embodied in computer-readable program code logic means, for performing the specified functions. It will also be understood that each block of the flowchart illustrations, algorithms, formulae, or computational depictions and combinations thereof described herein, can be implemented by special purpose hardware-based computer systems which perform the specified functions or steps, or combinations of special purpose hardware and computer-readable program code logic means.

Furthermore, these computer program instructions, such as embodied in computer-readable program code logic, may also be stored in a computer-readable memory that can direct a computer or other programmable processing apparatus to function in a particular manner, such that the instructions stored in the computer-readable memory produce an article of manufacture including instruction means which implement the function specified in the block(s) of the flowchart(s). The computer program instructions may also be loaded onto a computer or other programmable processing apparatus to cause a series of operational steps to be performed on the computer or other programmable processing apparatus to produce a computer-implemented process such that the instructions which execute on the computer or other programmable processing apparatus provide steps for implementing the functions specified in the block(s) of the flowchart(s), algorithm(s), formula(e), or computational depiction(s).

It will further be appreciated that the terms "programming" or "program executable" as used herein refer to one or more instructions that can be executed by a processor to perform a function as described herein. The instructions can be embodied in software, in firmware, or in a combination of software and firmware. The instructions can be stored local to the device in non-transitory media, or can be stored remotely such as on a server, or all or a portion of the instructions can be stored locally and remotely. Instructions stored remotely can be downloaded (pushed) to the device by user initiation, or automatically based on one or more factors. It will further be appreciated that as used herein, that the terms processor, computer processor, central processing unit (CPU), and computer are used synonymously to denote a device capable of executing the instructions and communicating with input/output interfaces and/or peripheral devices.

From the description herein, it will be appreciated that that the present disclosure encompasses multiple embodiments which include, but are not limited to, the following:

1. An apparatus for deformable image registration (DIR) of a target anatomy, the apparatus comprising: (a) a computer processor; and (b) a non-transitory computer-readable memory storing instructions executable by the computer processor; (c) wherein said instructions, when executed by the computer processor, perform steps comprising: (i) generating a high-resolution deformable biomechanical model from CT data acquired from a plurality of patient CT images of the target anatomy; (ii) simulating one or more deformations within said biomechanical model, the one or more deformations representing a range of inter-fraction patient posture changes and physiological regression; and (iii) generating modified CT images representing a deformed state of the target anatomy.

2. The apparatus of any preceding embodiment, wherein the target anatomy comprises a head and neck region of the patient and the biomechanical model is generated using one or more inter-fraction kVCT datasets and the corresponding structure contours of the head and neck region.

3. The apparatus of any preceding embodiment, wherein generating a high-resolution deformable biomechanical model comprises: assigning voxels within the CT images to corresponding single structures as a function of contoured vertices within the CT images; generating series of connected mass elements with associated mass-spring-damping (MSD) connections, each mass element being located at a center of each voxel; and connecting one or more mass elements with other mass elements via a spring damper formulation to ensure deformation of the one or mass elements in a specified physiological manner.

4. The apparatus of any preceding embodiment, wherein voxels inside a given 3D contour boundary are assigned and clustered using a GPU-based algorithm.

5. The apparatus of any preceding embodiment: wherein bony anatomy within the CT images is modeled as rigid body and muscle and soft tissue structures are modeled as MSD models with elastic material properties that corresponded to the underlying contoured anatomies; and
   wherein simulating the one or more deformations comprises computing the biomechanical head and neck model deformations and actuating the biomechanical head and neck model to represent posture changes and physiological changes.

6. The apparatus of any preceding embodiment, wherein head and neck deformations are configured to be actuated by user-defined rigid transformations of one or more skeletal structures.

7. The apparatus of any preceding embodiment, wherein computing the biomechanical head and neck model deformations comprises: calculating internal corrective forces on each mass element as a summation of tensile spring force, shear spring force, and a dashpot damping force; and updating the locations of each mass element from a previous iteration.

8. The apparatus of any preceding embodiment: wherein soft-tissue deformation for a given skeletal actuation is performed using an implicit Euler integration; and wherein each iteration of the Euler integration is split into individual iterative steps for the muscle structures and remaining soft tissue structures.

9. The apparatus of any preceding embodiment: wherein the one or more skeletal structures are modeled as rigid body; and wherein the muscle and soft tissue structures are modeled as mass spring models with elastic material properties that correspond to underlying contoured anatomies.

10. The apparatus of any preceding embodiment, wherein within a given muscle structure, the voxels are classified using a uniform grid, and a normalized mass is assigned to each voxel based on its Hounsfield number.

11. The apparatus of any preceding embodiment, wherein posture changes are simulated by articulating the one or more skeletal structures and enabling the soft structures to deform accordingly.

12. The apparatus of any preceding embodiment: wherein physiological regression comprises a tumor regression; and wherein said physiological regression is simulated by reducing a target volume and enabling surrounding soft tissue structures to deform accordingly.

13. The apparatus of any preceding embodiment: wherein the modified CT images comprise a 3D contour boundary having one or more of inconsistencies and gaps; and wherein voxels inside a given 3D contour boundary are clustered to form a deformable volumetric structure to account for the one or more of inconsistencies and gaps.

14. The apparatus of any preceding embodiment: wherein the processor comprises a graphics processing unit (GPU); wherein the simulations of posture changes and physiological regressions are performed at interactive speeds.

15. A method for deformable image registration (DIR) of a target anatomy, the method comprising: (a) generating a high-resolution deformable biomechanical model from CT data acquired from a plurality of patient CT images of the target anatomy; (b) simulating one or more deformations within said biomechanical model, the one or more deformations representing a range of inter-fraction patient posture changes and physiological regression; and (c) generating modified CT images representing a deformed state of the target anatomy; (d) wherein said method is performed by instructions executable by a computer processor and are stored on a non-transitory computer-readable memory.

16. The method of any preceding embodiment, wherein the target anatomy comprises a head and neck region of the patient and the biomechanical model is generated using one or more inter-fraction kVCT datasets and the corresponding structure contours of the head and neck region.

17. The method of any preceding embodiment, wherein generating a high-resolution deformable biomechanical model comprises: assigning voxels within the CT images to corresponding single structures as a function of contoured vertices within the CT images; generating series of connected mass elements with associated mass-spring-damping (MSD) connections, each mass element being located at a center of each voxel; and connecting one or more mass elements with other mass elements via a spring damper formulation to ensure deformation of the one or mass elements in a specified physiological manner.

18. The method of any preceding embodiment, wherein voxels inside a given 3D contour boundary are assigned and clustered using a GPU-based algorithm.

19. The method of any preceding embodiment: wherein bony anatomy within the CT images is modeled as rigid body and muscle and soft tissue structures are modeled as MSD models with elastic material properties that corresponded to the underlying contoured anatomies; and wherein simulating the one or more deformations comprises computing the biomechanical head and neck model deformations and actuating the biomechanical head and neck model to represent posture and physiological changes.

20. The method of any preceding embodiment, wherein head and neck deformations are configured to be actuated by user-defined rigid transformations of one or more skeletal structures.

21. The method of any preceding embodiment, wherein computing the biomechanical head and neck model deformations comprises: calculating internal corrective forces on each mass element as a summation of tensile spring force, shear spring force, and a dashpot damping force; and updating the locations of each mass element from a previous iteration.

22. The method of any preceding embodiment: wherein soft-tissue deformation for a given skeletal actuation is performed using an implicit Euler integration; and wherein each iteration of the Euler integration is split into individual iterative steps for the muscle structures and remaining soft tissue structures.

23. The method of any preceding embodiment: wherein the one or more skeletal structures are modeled as rigid body; and wherein the muscle and soft tissue structures are modeled as mass spring models with elastic material properties that corresponded to underlying contoured anatomies.

24. The method of any preceding embodiment, wherein within a given muscle structure, the voxels are classified using a uniform grid, and a normalized mass is assigned to each voxel based on its Hounsfield number.

25. The method of any preceding embodiment, wherein posture changes are simulated by articulating the skeletal structure and enabling the soft structures to deform accordingly.

26. The method of any preceding embodiment: wherein physiological regression comprises a tumor regression; and wherein said physiological regression is simulated by reducing the target volume and enabling surrounding soft structures to deform accordingly.

27. The method of any preceding embodiment: wherein the modified CT images comprise a 3D contour boundary having one or more of inconsistencies and gaps; and wherein voxels inside a given 3D contour boundary are clustered to form a deformable volumetric structure to account for the one or more of inconsistencies and gaps.

28. The method of any preceding embodiment: wherein the processor comprises a graphics processing unit (GPU); wherein the simulations of posture changes and physiological regressions are performed at interactive speeds.

Although the description herein contains many details, these should not be construed as limiting the scope of the disclosure but as merely providing illustrations of some of the presently preferred embodiments. Therefore, it will be appreciated that the scope of the disclosure fully encompasses other embodiments which may become obvious to those skilled in the art.

In the claims, reference to an element in the singular is not intended to mean "one and only one" unless explicitly so stated, but rather "one or more." All structural, chemical, and functional equivalents to the elements of the disclosed embodiments that are known to those of ordinary skill in the art are expressly incorporated herein by reference and are intended to be encompassed by the present claims. Furthermore, no element, component, or method step in the present disclosure is intended to be dedicated to the public regardless of whether the element, component, or method step is explicitly recited in the claims. No claim element herein is to be construed as a "means plus function" element unless the element is expressly recited using the phrase "means for". No claim element herein is to be construed as a "step

TABLE 1

Normalized color-coding scheme used for representing the strain. R, G, and B represent the red, green, and blue color channels.

| Displacement (mm) | R | G | B |
|---|---|---|---|
| −9.9 | 0.0 | 0.0 | 1.0 |
| −6.6 | 0.0 | 0.5 | 1.0 |
| −3.3 | 0.0 | 1.0 | 1.0 |
| 0 | 0.0 | 1.0 | 0.0 |
| 3.3 | 1.0 | 1.0 | 0.0 |
| 6.6 | 1.0 | 0.5 | 0.0 |
| 9.9 | 1.0 | 0.0 | 0.0 |

What is claimed is:

1. An apparatus for deformable image registration (DIR) of a target anatomy, the apparatus comprising:
   (a) a computer processor; and
   (b) a non-transitory computer-readable memory storing instructions executable by the computer processor;
   (c) wherein said instructions, when executed by the computer processor, perform steps comprising:
      (i) generating a high-resolution deformable biomechanical model from CT data acquired from a plurality of patient CT images of the target anatomy;
      (ii) simulating one or more deformations within said biomechanical model, the one or more deformations representing a range of inter-fraction patient posture changes and physiological regression; and
      (iii) generating modified CT images representing a deformed state of the target anatomy;
      (iv) wherein the target anatomy comprises a head and neck region of the patient and the biomechanical model is generated using one or more inter-fraction kVCT datasets and the corresponding structure contours of the head and neck region;
      (v) wherein generating a high-resolution deformable biomechanical model comprises:
         assigning voxels within the CT images to corresponding single structures as a function of contoured vertices within the CT images;
         generating series of connected mass elements with associated mass-spring-damping (MSD) connections, each mass element being located at a center of each voxel;
         connecting one or more mass elements with other mass elements via a spring damper formulation to ensure deformation of the one or mass elements in a specified physiological manner;
      (vi) wherein bony anatomy within the CT images is modeled as rigid body and muscle and soft tissue structures are modeled as MSD models with elastic material properties that corresponded to the underlying contoured anatomies;
      (vii) wherein simulating the one or more deformations comprises computing the biomechanical head and neck model deformations and actuating the biomechanical head and neck model to represent posture changes and physiological changes;
      (viii) wherein computing the biomechanical head and neck model deformations comprises:
         calculating internal corrective forces on each mass element as a summation of tensile spring force, shear spring force, and a dashpot damping force; and
         updating the locations of each mass element from a previous iteration.

2. The apparatus of claim 1, wherein voxels inside a given 3D contour boundary are assigned and clustered using a GPU-based algorithm.

3. The apparatus of claim 1, wherein head and neck deformations are configured to be actuated by user-defined rigid transformations of one or more skeletal structures.

4. The apparatus of claim 3:
   wherein soft-tissue deformation for a given skeletal actuation is performed using an implicit Euler integration; and
   wherein each iteration of the Euler integration is split into individual iterative steps for the muscle structures and remaining soft tissue structures.

5. The apparatus of claim 4:
   wherein the one or more skeletal structures are modeled as rigid body; and
   wherein the muscle and soft tissue structures are modeled as mass spring models with elastic material properties that correspond to underlying contoured anatomies.

6. The apparatus of claim 4, wherein within a given muscle structure, the voxels are classified using a uniform grid, and a normalized mass is assigned to each voxel based on its Hounsfield number.

7. The apparatus of claim 5, wherein posture changes are simulated by articulating the one or more skeletal structures and enabling the soft structures to deform accordingly.

8. The apparatus of claim 1:
   wherein physiological regression comprises a tumor regression; and
   wherein said physiological regression is simulated by reducing a target volume and enabling surrounding soft tissue structures to deform accordingly.

9. The apparatus of claim 1:
   wherein the modified CT images comprise a 3D contour boundary having one or more of inconsistencies and gaps; and
   wherein voxels inside a given 3D contour boundary are clustered to form a deformable volumetric structure to account for the one or more of inconsistencies and gaps.

10. The apparatus of claim 1:
    wherein the processor comprises a graphics processing unit (GPU);
    wherein the simulations of posture changes and physiological regressions are performed at interactive speeds.

11. A method for deformable image registration (DIR) of a target anatomy, the method comprising:
    (a) generating a high-resolution deformable biomechanical model from CT data acquired from a plurality of patient CT images of the target anatomy;
    (b) simulating one or more deformations within said biomechanical model, the one or more deformations representing a range of inter-fraction patient posture changes and physiological regression; and
    (c) generating modified CT images representing a deformed state of the target anatomy;
    (d) wherein the target anatomy comprises a head and neck region of the patient and the biomechanical model is generated using one or more inter-fraction kVCT datasets and the corresponding structure contours of the head and neck region;
    (e) wherein generating a high-resolution deformable biomechanical model comprises:

(i) assigning voxels within the CT images to corresponding single structures as a function of contoured vertices within the CT images;
generating series of connected mass elements with associated mass-spring-damping (MSD) connections, each mass element being located at a center of each voxel;
(ii) connecting one or more mass elements with other mass elements via a spring damper formulation to ensure deformation of the one or mass elements in a specified physiological manner;
(f) wherein bony anatomy within the CT images is modeled as rigid body and muscle and soft tissue structures are modeled as MSD models with elastic material properties that corresponded to the underlying contoured anatomies;
(g) wherein simulating the one or more deformations comprises computing the biomechanical head and neck model deformations and actuating the biomechanical head and neck model to represent posture changes and physiological changes;
(h) wherein computing the biomechanical head and neck model deformations comprises:
(i) calculating internal corrective forces on each mass element as a summation of tensile spring force, shear spring force, and a dashpot damping force; and
(ii) updating the locations of each mass element from a previous iteration;
(i) wherein said method is performed by instructions executable by a computer processor and are stored on a non-transitory computer-readable memory.

12. The method of claim 11, wherein voxels inside a given 3D contour boundary are assigned and clustered using a GPU-based algorithm.

13. The method of claim 11, wherein head and neck deformations are configured to be actuated by user-defined rigid transformations of one or more skeletal structures.

14. The method of claim 13:
wherein soft-tissue deformation for a given skeletal actuation is performed using an implicit Euler integration; and
wherein each iteration of the Euler integration is split into individual iterative steps for the muscle structures and remaining soft tissue structures.

15. The method of claim 14:
wherein the one or more skeletal structures are modeled as rigid body; and
wherein the muscle and soft tissue structures are modeled as mass spring models with elastic material properties that corresponded to underlying contoured anatomies.

16. The method of claim 14, wherein within a given muscle structure, the voxels are classified using a uniform grid, and a normalized mass is assigned to each voxel based on its Hounsfield number.

17. The method of claim 13, wherein posture changes are simulated by articulating the skeletal structure and enabling the soft structures to deform accordingly.

18. The method of claim 11:
wherein physiological regression comprises a tumor regression; and
wherein said physiological regression is simulated by reducing the target volume and enabling surrounding soft structures to deform accordingly.

19. The method of claim 11:
wherein the modified CT images comprise a 3D contour boundary having one or more of inconsistencies and gaps; and wherein voxels inside a given 3D contour boundary are clustered to form a deformable volumetric structure to account for the one or more of inconsistencies and gaps.

20. The method of claim 11:
wherein the processor comprises a graphics processing unit (GPU);
wherein the simulations of posture changes and physiological regressions are performed at interactive speeds.

21. An apparatus for deformable image registration (DIR) of a target anatomy, the apparatus comprising:
(a) a computer processor; and
(b) a non-transitory computer-readable memory storing instructions executable by the computer processor;
(c) wherein said instructions, when executed by the computer processor, perform steps comprising:
(i) generating a high-resolution deformable biomechanical model from CT data acquired from a plurality of patient CT images of the target anatomy;
(ii) simulating one or more deformations within said biomechanical model, the one or more deformations representing a range of inter-fraction patient posture changes and physiological regression; and
(iii) generating modified CT images representing a deformed state of the target anatomy;
(iv) wherein the target anatomy comprises a head and neck region of the patient and the biomechanical model is generated using one or more inter-fraction kVCT datasets and the corresponding structure contours of the head and neck region;
(v) wherein generating a high-resolution deformable biomechanical model comprises:
assigning voxels within the CT images to corresponding single structures as a function of contoured vertices within the CT images;
generating series of connected mass elements with associated mass-spring-damping (MSD) connections, each mass element being located at a center of each voxel;
connecting one or more mass elements with other mass elements via a spring damper formulation to ensure deformation of the one or mass elements in a specified physiological manner;
(vi) wherein bony anatomy within the CT images is modeled as rigid body and muscle and soft tissue structures are modeled as MSD models with elastic material properties that corresponded to the underlying contoured anatomies;
(vii) wherein simulating the one or more deformations comprises computing the biomechanical head and neck model deformations and actuating the biomechanical head and neck model to represent posture changes and physiological changes;
(viii) wherein head and neck deformations are configured to be actuated by user-defined rigid transformations of one or more skeletal structures;
(viii) wherein soft-tissue deformation for a given skeletal actuation is performed using an implicit Euler integration; and
(ix) wherein each iteration of the Euler integration is split into individual iterative steps for the muscle structures and remaining soft tissue structures.

22. An apparatus for deformable image registration (DIR) of a target anatomy, the apparatus comprising:
(a) a computer processor; and
(b) a non-transitory computer-readable memory storing instructions executable by the computer processor;
(c) wherein said instructions, when executed by the computer processor, perform steps comprising:
(i) generating a high-resolution deformable biomechanical model from CT data acquired from a plurality of patient CT images of the target anatomy;
(ii) simulating one or more deformations within said biomechanical model, the one or more deformations representing a range of inter-fraction patient posture changes and physiological regression; and
(iii) generating modified CT images representing a deformed state of the target anatomy;
(iv) wherein the target anatomy comprises a head and neck region of the patient and the biomechanical model is generated using one or more inter-fraction kVCT datasets and the corresponding structure contours of the head and neck region;
(v) wherein generating a high-resolution deformable biomechanical model comprises:
assigning voxels within the CT images to corresponding single structures as a function of contoured vertices within the CT images;
generating series of connected mass elements with associated mass-spring-damping (MSD) connections, each mass element being located at a center of each voxel;
connecting one or more mass elements with other mass elements via a spring damper formulation to ensure deformation of the one or mass elements in a specified physiological manner;
(vi) wherein bony anatomy within the CT images is modeled as rigid body and muscle and soft tissue structures are modeled as MSD models with elastic material properties that corresponded to the underlying contoured anatomies;
(vii) wherein simulating the one or more deformations comprises computing the biomechanical head and neck model deformations and actuating the biomechanical head and neck model to represent posture changes and physiological changes;
(viii) wherein physiological regression comprises a tumor regression; and
(ix) wherein said physiological regression is simulated by reducing a target volume and enabling surrounding soft tissue structures to deform accordingly.

23. A method for deformable image registration (DIR) of a target anatomy, the method comprising:
(a) generating a high-resolution deformable biomechanical model from CT data acquired from a plurality of patient CT images of the target anatomy;
(b) simulating one or more deformations within said biomechanical model, the one or more deformations representing a range of inter-fraction patient posture changes and physiological regression; and
(c) generating modified CT images representing a deformed state of the target anatomy;
(d) wherein the target anatomy comprises a head and neck region of the patient and the biomechanical model is generated using one or more inter-fraction kVCT datasets and the corresponding structure contours of the head and neck region;
(e) wherein generating a high-resolution deformable biomechanical model comprises:
(i) assigning voxels within the CT images to corresponding single structures as a function of contoured vertices within the CT images;
(ii) generating series of connected mass elements with associated mass-spring-damping (MSD) connections, each mass element being located at a center of each voxel;
(iii) connecting one or more mass elements with other mass elements via a spring damper formulation to ensure deformation of the one or mass elements in a specified physiological manner;
(f) wherein bony anatomy within the CT images is modeled as rigid body and muscle and soft tissue structures are modeled as MSD models with elastic material properties that corresponded to the underlying contoured anatomies;
(g) wherein simulating the one or more deformations comprises computing the biomechanical head and neck model deformations and actuating the biomechanical head and neck model to represent posture changes and physiological changes;
(h) wherein head and neck deformations are configured to be actuated by user-defined rigid transformations of one or more skeletal structures;
(i) wherein soft-tissue deformation for a given skeletal actuation is performed using an implicit Euler integration; and
(j) wherein each iteration of the Euler integration is split into individual iterative steps for the muscle structures and remaining soft tissue structures;
(k) wherein said method is performed by instructions executable by a computer processor and are stored on a non-transitory computer-readable memory.

24. A method for deformable image registration (DIR) of a target anatomy, the method comprising:
(a) generating a high-resolution deformable biomechanical model from CT data acquired from a plurality of patient CT images of the target anatomy;
(b) simulating one or more deformations within said biomechanical model, the one or more deformations representing a range of inter-fraction patient posture changes and physiological regression; and
(c) generating modified CT images representing a deformed state of the target anatomy;
(d) wherein the target anatomy comprises a head and neck region of the patient and the biomechanical model is generated using one or more inter-fraction kVCT datasets and the corresponding structure contours of the head and neck region;
(e) wherein generating a high-resolution deformable biomechanical model comprises:
(i) assigning voxels within the CT images to corresponding single structures as a function of contoured vertices within the CT images;
(ii) generating series of connected mass elements with associated mass-spring-damping (MSD) connections, each mass element being located at a center of each voxel;
(iii) connecting one or more mass elements with other mass elements via a spring damper formulation to ensure deformation of the one or mass elements in a specified physiological manner;
(f) wherein bony anatomy within the CT images is modeled as rigid body and muscle and soft tissue structures are modeled as MSD models with elastic material properties that corresponded to the underlying contoured anatomies;

(h) wherein simulating the one or more deformations comprises computing the biomechanical head and neck model deformations and actuating the biomechanical head and neck model to represent posture changes and physiological changes;
(i) wherein physiological regression comprises a tumor regression; and
(j) wherein said physiological regression is simulated by reducing a target volume and enabling surrounding soft tissue structures to deform accordingly;
(k) wherein said method is performed by instructions executable by a computer processor and are stored on a non-transitory computer-readable memory.

\* \* \* \* \*